(12) United States Patent
Li et al.

(10) Patent No.: US 8,703,917 B2
(45) Date of Patent: Apr. 22, 2014

(54) EPIDERMAL GROWTH FACTOR RECEPTOR VARIANTS AND PHARMACEUTICAL COMPOSITIONS THEREOF

(75) Inventors: Zonghai Li, Shanghai (CN); Hai Wang, Shanghai (CN); Min Zhou, Shanghai (CN); Xiaorong Pan, Shanghai (CN); Jianren Gu, Shanghai (CN); Shengli Yang, Shanghai (CN)

(73) Assignee: Shanghai Cancer Institute, Shanghai (CN)

(*) Notice: Subject to any disclaimer, the term of this patent is extended or adjusted under 35 U.S.C. 154(b) by 0 days.

(21) Appl. No.: 13/575,432

(22) PCT Filed: Jan. 26, 2011

(86) PCT No.: PCT/CN2011/000121
§ 371 (c)(1),
(2), (4) Date: Oct. 12, 2012

(87) PCT Pub. No.: WO2011/091716
PCT Pub. Date: Aug. 4, 2011

(65) Prior Publication Data
US 2013/0034558 A1    Feb. 7, 2013

(30) Foreign Application Priority Data
Jan. 26, 2010  (CN) .......................... 2010 1 0100949

(51) Int. Cl.
*C07K 1/00*    (2006.01)
*C07K 14/00*   (2006.01)
*C07K 17/00*   (2006.01)
*A61K 38/22*   (2006.01)
*C07K 14/485*  (2006.01)

(52) U.S. Cl.
USPC .......................................... 530/350; 514/9.6

(58) Field of Classification Search
None
See application file for complete search history.

(56) References Cited

U.S. PATENT DOCUMENTS 6,790,614 B1 * 9/2004 Pippig et al. ................. 435/6.14

OTHER PUBLICATIONS

GenBank Accession No. ADL28125, version ADL28125.1, dated Jan. 1, 2011 (retrieved from Protein database at www.ncbi.nlm.nih.gov on Mar. 23, 2011), (3 pages).
NCBI Reference Sequence Accession No. XP_001107305, version XP_001107305.1, dated Jun. 14, 2006 (retrieved from Protein database at www.ncbi.nlm.nih.gov on Mar. 23, 2011), (3 pages).
International Search Report for international application No. PCT/CN2011/000121, dated Apr. 21, 2011 (6 pages).

* cited by examiner

*Primary Examiner* — Robert Landsman
(74) *Attorney, Agent, or Firm* — Hamre, Schumann, Mueller & Larson, P.C.

(57) ABSTRACT

Provided are a novel Epidermal growth factor receptor variant-EGFRvA protein, a polynucleotide encoding the EGFRvA protein and a method of preparing the EGFRvA protein via recombination technology. Also provided is a uses of the polynucleotide encoding the EGFRvA protein. The EGFRvA protein has a function of promoting tumor cell invasion or promoting tumor cell migration.

3 Claims, 8 Drawing Sheets

SEQUENCE LISTING

```
<160> NUMBER OF SEQ ID NOS: 19

<210> SEQ ID NO 1
<211> LENGTH: 3763
<212> TYPE: DNA
<213> ORGANISM: Homo sapiens
<220> FEATURE:
<221> NAME/KEY: CDS
<222> LOCATION: (44)..(3454)

<400> SEQUENCE: 1
gtattgatcg ggagagccgg agcgagctct tcggggagca gcg atg cga ccc tcc        55
                                              Met Arg Pro Ser
                                              1 ggg acg gcc ggg gca gcg ctc ctg gcg ctg ctg gct gcg ctc tgc ccg       103
Gly Thr Ala Gly Ala Ala Leu Leu Ala Leu Leu Ala Ala Leu Cys Pro
5                   10                  15                  20 gcg agt cgg gct ctg gag gaa aag aaa gtt tgc caa ggc acg agt aac       151
Ala Ser Arg Ala Leu Glu Glu Lys Lys Val Cys Gln Gly Thr Ser Asn
                25                  30                  35 aag ctc acg cag ttg ggc act ttt gaa gat cat ttt ctc agc ctc cag       199
Lys Leu Thr Gln Leu Gly Thr Phe Glu Asp His Phe Leu Ser Leu Gln
            40                  45                  50 agg atg ttc aat aac tgt gag gtg gtc ctt ggg aat ttg gaa att acc       247
Arg Met Phe Asn Asn Cys Glu Val Val Leu Gly Asn Leu Glu Ile Thr
        55                  60                  65 tat gtg cag agg aat tat gat ctt tcc ttc tta aag acc atc cag gag       295
Tyr Val Gln Arg Asn Tyr Asp Leu Ser Phe Leu Lys Thr Ile Gln Glu
    70                  75                  80 gtg gct ggt tat gtc ctc att gcc ctc aac aca gtg gag cga att cct       343
```

```
Val Ala Gly Tyr Val Leu Ile Ala Leu Asn Thr Val Glu Arg Ile Pro
 85                  90                  95                 100 ttg gaa aac ctg cag atc atc aga gga aat atg tac tac gaa aat tcc       391
Leu Glu Asn Leu Gln Ile Ile Arg Gly Asn Met Tyr Tyr Glu Asn Ser
                105                 110                 115 tat gcc tta gca gtc tta tct aac tat gat gca aat aaa acc gga ctg       439
Tyr Ala Leu Ala Val Leu Ser Asn Tyr Asp Ala Asn Lys Thr Gly Leu
                120                 125                 130 aag gag ctg ccc atg aga aat tta cag gaa atc ctg cat ggc gcc gtg       487
Lys Glu Leu Pro Met Arg Asn Leu Gln Glu Ile Leu His Gly Ala Val
                135                 140                 145 cgg ttc agc aac aac cct gcc ctg tgc aac gtg gag agc atc cag tgg       535
Arg Phe Ser Asn Asn Pro Ala Leu Cys Asn Val Glu Ser Ile Gln Trp
        150                 155                 160 cgg gac ata gtc agc agt gac ttt ctc agc aac atg tcg atg gac ttc       583
Arg Asp Ile Val Ser Ser Asp Phe Leu Ser Asn Met Ser Met Asp Phe
165                 170                 175                 180 cag aac cac ctg ggc agc tgc caa aag tgt gat cca agc tgt ccc aat       631
Gln Asn His Leu Gly Ser Cys Gln Lys Cys Asp Pro Ser Cys Pro Asn
                185                 190                 195 ggg agc tgc tgg ggt gca gga gag gag aac tgc cag aaa ctg acc aaa       679
Gly Ser Cys Trp Gly Ala Gly Glu Glu Asn Cys Gln Lys Leu Thr Lys
                200                 205                 210 atc atc tgt gcc cag cag tgt tcc ggg cgc tgc cgt ggc aag tcc ccc       727
Ile Ile Cys Ala Gln Gln Cys Ser Gly Arg Cys Arg Gly Lys Ser Pro
                215                 220                 225 agt gac tgc tgc cac aac cag tgt gct gca ggc tgc aca ggc ccc cgg       775
Ser Asp Cys Cys His Asn Gln Cys Ala Ala Gly Cys Thr Gly Pro Arg
        230                 235                 240 gag agc gac tgc ctg gtc tgc cgc aaa ttc cga gac gaa gcc acg tgc       823
Glu Ser Asp Cys Leu Val Cys Arg Lys Phe Arg Asp Glu Ala Thr Cys
245                 250                 255                 260 aag gac acc tgc ccc cca ctc atg ctc tac aac ccc acc acg tac cag       871
Lys Asp Thr Cys Pro Pro Leu Met Leu Tyr Asn Pro Thr Thr Tyr Gln
                265                 270                 275 atg gat gtg aac ccc gag ggc aaa tac agc ttt ggt gcc acc tgc gtg       919
Met Asp Val Asn Pro Glu Gly Lys Tyr Ser Phe Gly Ala Thr Cys Val
                280                 285                 290 aag aag tgt ccc cgt aat tat gtg gtg aca gat cac ggc tcg tgc gtc       967
Lys Lys Cys Pro Arg Asn Tyr Val Val Thr Asp His Gly Ser Cys Val
                295                 300                 305 cga gcc tgt ggg gcc gac agc tat gag atg gag gaa gac ggc gtc cgc       1015
Arg Ala Cys Gly Ala Asp Ser Tyr Glu Met Glu Glu Asp Gly Val Arg
                310                 315                 320 aag tgt aag aag tgc gaa ggg cct tgc cgc aaa gtg tgt aac gga ata       1063
Lys Cys Lys Lys Cys Glu Gly Pro Cys Arg Lys Val Cys Asn Gly Ile
325                 330                 335                 340 ggt att ggt gaa ttt aaa gac tca ctc tcc ata aat gct acg aat att       1111
Gly Ile Gly Glu Phe Lys Asp Ser Leu Ser Ile Asn Ala Thr Asn Ile
                345                 350                 355 aaa cac ttc aaa aac tgc acc tcc atc agt ggc gat ctc cac atc ctg       1159
Lys His Phe Lys Asn Cys Thr Ser Ile Ser Gly Asp Leu His Ile Leu
                360                 365                 370 ccg gtg gca ttt agg ggt gac tcc ttc aca cat act cct cct ctg gat       1207
Pro Val Ala Phe Arg Gly Asp Ser Phe Thr His Thr Pro Pro Leu Asp
                375                 380                 385 cca cag gaa ctg gat att ctg aaa acc gta aag gaa atc aca ggg ttt       1255
Pro Gln Glu Leu Asp Ile Leu Lys Thr Val Lys Glu Ile Thr Gly Phe
        390                 395                 400 ttg ctg att cag gct tgg cct gaa aac agg acg gac ctc cat gcc ttt       1303
```

```
Leu Leu Ile Gln Ala Trp Pro Glu Asn Arg Thr Asp Leu His Ala Phe
405             410                 415                 420 gag aac cta gaa atc ata cgc ggc agg acc aag caa cat ggt cag ttt    1351
Glu Asn Leu Glu Ile Ile Arg Gly Arg Thr Lys Gln His Gly Gln Phe
                    425                 430                 435 tct ctt gca gtc gtc agc ctg aac ata aca tcc ttg gga tta cgc tcc    1399
Ser Leu Ala Val Val Ser Leu Asn Ile Thr Ser Leu Gly Leu Arg Ser
                440                 445                 450 ctc aag gag ata agt gat gga gat gtg ata att tca gga aac aaa aat    1447
Leu Lys Glu Ile Ser Asp Gly Asp Val Ile Ile Ser Gly Asn Lys Asn
            455                 460                 465 ttg tgc tat gca aat aca ata aac tgg aaa aaa ctg ttt ggg acc tcc    1495
Leu Cys Tyr Ala Asn Thr Ile Asn Trp Lys Lys Leu Phe Gly Thr Ser
        470                 475                 480 ggt cag aaa acc aaa att ata agc aac aga ggt gaa aac agc tgc aag    1543
Gly Gln Lys Thr Lys Ile Ile Ser Asn Arg Gly Glu Asn Ser Cys Lys
485                 490                 495                 500 gcc aca ggc cag gtc tgc cat gcc ttg tgc tcc ccc gag ggc tgc tgg    1591
Ala Thr Gly Gln Val Cys His Ala Leu Cys Ser Pro Glu Gly Cys Trp
                    505                 510                 515 ggc ccg gag ccc agg gac tgc gtc tct tgc cgg aat gtc agc cga ggc    1639
Gly Pro Glu Pro Arg Asp Cys Val Ser Cys Arg Asn Val Ser Arg Gly
                520                 525                 530 agg gaa tgc gtg gac aag tgc aac ctt ctg gag ggt gag cca agg gag    1687
Arg Glu Cys Val Asp Lys Cys Asn Leu Leu Glu Gly Glu Pro Arg Glu
            535                 540                 545 ttt gtg gag aac tct gag tgc ata cag tgc cac cca gag tgc ctg cct    1735
Phe Val Glu Asn Ser Glu Cys Ile Gln Cys His Pro Glu Cys Leu Pro
        550                 555                 560 cag gcc atg aac atc acc tgc aca gga cgg gga cca gac aac tgt atc    1783
Gln Ala Met Asn Ile Thr Cys Thr Gly Arg Gly Pro Asp Asn Cys Ile
565                 570                 575                 580 cag tgt gcc cac tac att gac ggc ccc cac tgc gtc aag acc tgc ccg    1831
Gln Cys Ala His Tyr Ile Asp Gly Pro His Cys Val Lys Thr Cys Pro
                    585                 590                 595 gca gga gtc atg gga gaa aac aac acc ctg gtc tgg aag tac gca gac    1879
Ala Gly Val Met Gly Glu Asn Asn Thr Leu Val Trp Lys Tyr Ala Asp
                600                 605                 610 gcc ggc cat gtg tgc cac ctg tgc cat cca aac tgc acc tac gga tgc    1927
Ala Gly His Val Cys His Leu Cys His Pro Asn Cys Thr Tyr Gly Cys
            615                 620                 625 act ggg cca ggt ctt gaa ggc tgt cca acg aat ggg cct aag atc ccg    1975
Thr Gly Pro Gly Leu Glu Gly Cys Pro Thr Asn Gly Pro Lys Ile Pro
        630                 635                 640 tcc atc gcc act ggg atg gtg ggg gcc ctc ctc ttg ctg ctg gtg gtg    2023
Ser Ile Ala Thr Gly Met Val Gly Ala Leu Leu Leu Leu Leu Val Val
645                 650                 655                 660 gcc ctg ggg atc ggc ctc ttc atg cga agg cgc cac atc gtt cgg aag    2071
Ala Leu Gly Ile Gly Leu Phe Met Arg Arg Arg His Ile Val Arg Lys
                    665                 670                 675 cgc acg ctg cgg agg ctg ctg cag gag agg gag ctt gtg gag cct ctt    2119
Arg Thr Leu Arg Arg Leu Leu Gln Glu Arg Glu Leu Val Glu Pro Leu
                680                 685                 690 aca ccc agt gga gaa gct ccc aac caa gct ctc ttg agg atc ttg aag    2167
Thr Pro Ser Gly Glu Ala Pro Asn Gln Ala Leu Leu Arg Ile Leu Lys
            695                 700                 705 gaa act gaa ttc aaa aag atc aaa gtg ctg ggc tcc ggt gcg ttc ggc    2215
Glu Thr Glu Phe Lys Lys Ile Lys Val Leu Gly Ser Gly Ala Phe Gly
        710                 715                 720 acg gtg tat aag gga ctc tgg atc cca gaa ggt gag aaa gtt aaa att    2263
```

-continued

| | | |
|---|---|---|
| Thr Val Tyr Lys Gly Leu Trp Ile Pro Glu Gly Glu Lys Val Lys Ile<br>725                            730                        735                        740 | | |
| ccc gtc gct atc aag gaa tta aga gaa gca aca tct ccg aaa gcc aac<br>Pro Val Ala Ile Lys Glu Leu Arg Glu Ala Thr Ser Pro Lys Ala Asn<br>                    745                        750                        755 | | 2311 |
| aag gaa atc ctc gat gaa gcc tac gtg atg gcc agc gtg gac aac ccc<br>Lys Glu Ile Leu Asp Glu Ala Tyr Val Met Ala Ser Val Asp Asn Pro<br>                    760                        765                        770 | | 2359 |
| cac gtg tgc cgc ctg ctg ggc atc tgc ctc acc tcc acc gtg cag ctc<br>His Val Cys Arg Leu Leu Gly Ile Cys Leu Thr Ser Thr Val Gln Leu<br>                775                        780                        785 | | 2407 |
| atc acg cag ctc atg ccc ttc ggc tgc ctc ctg gac tat gtc cgg gaa<br>Ile Thr Gln Leu Met Pro Phe Gly Cys Leu Leu Asp Tyr Val Arg Glu<br>        790                        795                        800 | | 2455 |
| cac aaa gac aat att ggc tcc cag tac ctg ctc aac tgg tgt gtg cag<br>His Lys Asp Asn Ile Gly Ser Gln Tyr Leu Leu Asn Trp Cys Val Gln<br>805                            810                        815                        820 | | 2503 |
| atc gca aag ggc atg aac tac ttg gag gac cgt cgc ttg gtg cac cgc<br>Ile Ala Lys Gly Met Asn Tyr Leu Glu Asp Arg Arg Leu Val His Arg<br>                        825                        830                        835 | | 2551 |
| gac ctg gca gcc agg aac gta ctg gtg aaa aca ccg cag cat gtc aag<br>Asp Leu Ala Ala Arg Asn Val Leu Val Lys Thr Pro Gln His Val Lys<br>                840                        845                        850 | | 2599 |
| atc aca gat ttt ggg ctg gcc aaa ctg ctg ggt gcg gaa gag aaa gaa<br>Ile Thr Asp Phe Gly Leu Ala Lys Leu Leu Gly Ala Glu Glu Lys Glu<br>        855                        860                        865 | | 2647 |
| tac cat gca gaa gga ggc aaa gtg cct atc aag tgg atg gca ttg gaa<br>Tyr His Ala Glu Gly Gly Lys Val Pro Ile Lys Trp Met Ala Leu Glu<br>870                            875                        880 | | 2695 |
| tca att tta cac aga atc tat acc cac cag agt gat gtc tgg agc tac<br>Ser Ile Leu His Arg Ile Tyr Thr His Gln Ser Asp Val Trp Ser Tyr<br>885                            890                        895                        900 | | 2743 |
| ggg gtg acc gtt tgg gag ttg atg acc ttt gga tcc aag cca tat gac<br>Gly Val Thr Val Trp Glu Leu Met Thr Phe Gly Ser Lys Pro Tyr Asp<br>                        905                        910                        915 | | 2791 |
| gga atc cct gcc agc gag atc tcc tcc atc ctg gag aaa gga gaa cgc<br>Gly Ile Pro Ala Ser Glu Ile Ser Ser Ile Leu Glu Lys Gly Glu Arg<br>        920                        925                        930 | | 2839 |
| ctc cct cag cca ccc ata tgt acc atc gat gtc tac atg atc atg gtc<br>Leu Pro Gln Pro Pro Ile Cys Thr Ile Asp Val Tyr Met Ile Met Val<br>                935                        940                        945 | | 2887 |
| aag tgc tgg atg ata gac gca gat agt cgc cca aag ttc cgt gag ttg<br>Lys Cys Trp Met Ile Asp Ala Asp Ser Arg Pro Lys Phe Arg Glu Leu<br>        950                        955                        960 | | 2935 |
| atc atc gaa ttc tcc aaa atg gcc cga gac ccc cag cgc tac ctt gtc<br>Ile Ile Glu Phe Ser Lys Met Ala Arg Asp Pro Gln Arg Tyr Leu Val<br>965                            970                        975                        980 | | 2983 |
| att cag ggg gat gaa aga atg cat ttg cca agt cct aca gac tcc aac<br>Ile Gln Gly Asp Glu Arg Met His Leu Pro Ser Pro Thr Asp Ser Asn<br>                        985                        990                        995 | | 3031 |
| ttc tac cgt gcc ctg atg gat gaa gaa gac atg gac gac gtg gtg<br>Phe Tyr Arg Ala Leu Met Asp Glu Glu Asp Met Asp Asp Val Val<br>                    1000                 1005               1010 | | 3076 |
| gat gcc gac gag tac ctc atc cca cag cag ggc ttc ttc agc agc<br>Asp Ala Asp Glu Tyr Leu Ile Pro Gln Gln Gly Phe Phe Ser Ser<br>                    1015                 1020               1025 | | 3121 |
| ccc tcc acg tca cgg act ccc ctg ctg agc tct ctg agt gca acc<br>Pro Ser Thr Ser Arg Thr Pro Leu Leu Ser Ser Leu Ser Ala Thr<br>                    1030                 1035               1040 | | 3166 |
| agc aac aat tcc acc gtg gct tgc att gat aga aat ggg ctg caa<br> | | 3211 |

```
Ser Asn Asn Ser Thr Val Ala Cys Ile Asp Arg Asn Gly Leu Gln
            1045                1050                1055 agc tgt ccc atc aag gaa gac agc ttc ttg cag cga tac agc tca         3256
Ser Cys Pro Ile Lys Glu Asp Ser Phe Leu Gln Arg Tyr Ser Ser
            1060                1065                1070 gac ccc aca ggc gcc ttg act gag gac agc ata gac gac acc ttc         3301
Asp Pro Thr Gly Ala Leu Thr Glu Asp Ser Ile Asp Asp Thr Phe
            1075                1080                1085 ctc cca gtg cct ggt gag tgg ctt gtc tgg aaa cag tcc tgc tcc         3346
Leu Pro Val Pro Gly Glu Trp Leu Val Trp Lys Gln Ser Cys Ser
            1090                1095                1100 tca acc tcc tcg acc cac tca gca gca gcc agt ctc cag tgt cca         3391
Ser Thr Ser Ser Thr His Ser Ala Ala Ala Ser Leu Gln Cys Pro
            1105                1110                1115 agc cag gtg ctc cct cca gca tct cca gag ggg gaa aca gtg gca         3436
Ser Gln Val Leu Pro Pro Ala Ser Pro Glu Gly Glu Thr Val Ala
            1120                1125                1130 gat ttg cag aca cag tga agggcgtaag gagcagataa acacatgacc            3484
Asp Leu Gln Thr Gln
            1135 gagcctgcac aagctctttg ttgtgtctgg ttgtttgctg tacctctgtt gtaagaatga   3544 atctgcaaaa tttctagctt atgaagcaaa tcacggacat acacatctgt atgtgtgagt   3604 gttcatgatg tgtgtacatc tgtgtatgtg tgtgtgtgta tgtgtgtgtt tgtgacagat   3664 ttgatccctg ttctctctgc tggctctatc ttgacctgtg aaacgtatat taactaatt    3724 aaatattagt taatattaat aaaaaaaaaa aaaaaaaaa                          3763

<210> SEQ ID NO 2
<211> LENGTH: 1136
<212> TYPE: PRT
<213> ORGANISM: Homo sapiens

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190
```

```
Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
        210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
```

-continued

```
            610                 615                 620
Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg His
                660                 665                 670

Ile Val Arg Lys Arg Thr Leu Arg Arg Leu Leu Gln Glu Arg Glu Leu
                675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
                755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
                995                 1000                1005

Asp Val Val Asp Ala Asp Glu Tyr Leu Ile Pro Gln Gln Gly Phe
        1010                1015                1020

Phe Ser Ser Pro Ser Thr Ser Arg Thr Pro Leu Leu Ser Ser Leu
        1025                1030                1035
```

-continued

```
Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Gly Glu Trp Leu Val Trp Lys Gln
    1085                1090                1095

Ser Cys Ser Ser Thr Ser Ser Thr His Ser Ala Ala Ala Ser Leu
    1100                1105                1110

Gln Cys Pro Ser Gln Val Leu Pro Pro Ala Ser Pro Glu Gly Glu
    1115                1120                1125

Thr Val Ala Asp Leu Gln Thr Gln
    1130                1135

<210> SEQ ID NO 3
<211> LENGTH: 21
<212> TYPE: DNA
<213> ORGANISM: Homo sapiens

<400> SEQUENCE: 3 tccccctcctg agctctctga g                                           21

<210> SEQ ID NO 4
<211> LENGTH: 24
<212> TYPE: DNA
<213> ORGANISM: Homo sapiens

<400> SEQUENCE: 4
tgacttgata cagtaccgat ccgg                                         24

<210> SEQ ID NO 5
<211> LENGTH: 27
<212> TYPE: DNA
<213> ORGANISM: Homo sapiens

<400> SEQUENCE: 5
tgtacacaca tcatgaacac tcacaca                                      27

<210> SEQ ID NO 6
<211> LENGTH: 22
<212> TYPE: DNA
<213> ORGANISM: Homo sapiens

<400> SEQUENCE: 6
agtgcaacca gcaacaattc ca                                           22

<210> SEQ ID NO 7
<211> LENGTH: 24
<212> TYPE: DNA
<213> ORGANISM: Homo sapiens

<400> SEQUENCE: 7
ggaatcaagc atcctctgga agac                                         24

<210> SEQ ID NO 8
<211> LENGTH: 25
<212> TYPE: DNA
<213> ORGANISM: Homo sapiens

<400> SEQUENCE: 8
caacagaggt acagcaaaca accag                                        25
```

```
<210> SEQ ID NO 9
<211> LENGTH: 19
<212> TYPE: DNA
<213> ORGANISM: Homo sapiens

<400> SEQUENCE: 9
gtattgatcg ggagagccg                                                  19

<210> SEQ ID NO 10
<211> LENGTH: 24
<212> TYPE: DNA
<213> ORGANISM: Homo sapiens

<400> SEQUENCE: 10
tgacttgata cagtaccgat ccgg                                            24

<210> SEQ ID NO 11
<211> LENGTH: 27
<212> TYPE: DNA
<213> ORGANISM: Homo sapiens

<400> SEQUENCE: 11
tgtacacaca tcatgaacac tcacaca                                         27

<210> SEQ ID NO 12
<211> LENGTH: 18
<212> TYPE: DNA
<213> ORGANISM: Homo sapiens

<400> SEQUENCE: 12
atgcgaccct ccgggacg                                                   18

<210> SEQ ID NO 13
<211> LENGTH: 24
<212> TYPE: DNA
<213> ORGANISM: Homo sapiens

<400> SEQUENCE: 13
ggaatcaagc atcctctgga agac                                            24

<210> SEQ ID NO 14
<211> LENGTH: 25
<212> TYPE: DNA
<213> ORGANISM: Homo sapiens

<400> SEQUENCE: 14
caacagaggt acagcaaaca accag                                           25

<210> SEQ ID NO 15
<211> LENGTH: 22
<212> TYPE: PRT
<213> ORGANISM: Homo sapiens

<400> SEQUENCE: 15

Cys Ser Thr Ala Glu Asn Ala Glu Tyr Leu Arg Val Ala Pro Gln Ser
 1               5                  10                  15

Ser Glu Phe Ile Gly Ala
            20

<210> SEQ ID NO 16
<211> LENGTH: 22
<212> TYPE: PRT
<213> ORGANISM: Homo sapiens
```

-continued

```
<400> SEQUENCE: 16

Cys Pro Ser Gln Val Leu Pro Pro Ala Ser Pro Glu Gly Glu Thr Val
1               5                   10                  15

Ala Asp Lys Gln Thr Gln
            20

<210> SEQ ID NO 17
<211> LENGTH: 54
<212> TYPE: DNA
<213> ORGANISM: Polynucleotide

<400> SEQUENCE: 17
gccacaaagc agtgaattta ttcaagagat aaattcactg ctttgtggct tttt          54

<210> SEQ ID NO 18
<211> LENGTH: 58
<212> TYPE: DNA
<213> ORGANISM: Polynucleotide

<400> SEQUENCE: 18
gagcagccag tctccagtgt ccaatcaaga gttggacact ggagactggc tgcttttt     58

<210> SEQ ID NO 19
<211> LENGTH: 50
<212> TYPE: DNA
<213> ORGANISM: Polynucleotide

<400> SEQUENCE: 19
gtctccgaac gtgtcacgtt caagagacgt gacacgttcg gagactttt                50
```

EPIDERMAL GROWTH FACTOR RECEPTOR VARIANTS AND PHARMACEUTICAL COMPOSITIONS THEREOF

TECHNICAL FIELD

This invention relates to the field of biotechnology and medicine, and, in particular, relates to a novel polynucleotide encoding human EGFRvA (Epidermal growth factor receptor variant A, EGFRvA) and the polypeptide encoded by said polynucleotide. The invention also relates to the uses and preparation of these polynucleotides and polypeptides.

BACKGROUND

The epidermal growth factor receptor (EGFR) is the 170 kilodalton membrane glycoprotein product of the proto-oncogen c-erb B[1]. The EGFR gene is the cellular homolog of the erb B oncogene originally identified in avian erythroblastosis viruses[1-2]. Activation of this oncogene by gene amplification has been observed in a variety of human tumors[3-6].

EGFR has been demonstrated to be overexpressed on many types of human solid tumors[7], including lung, colon, breast, gastric, brain, bladder, head and neck, ovarian, kidney and prostate carcinomas[7]. One major difference between v-erb B oncogenes and the normal EGFR gene is that the viral oncogenes are amino-truncated versions of the normal receptor: they lack most of the extracytoplasmic domain but remain the transmembrane and tyrosine kinase domains[8-11]. This results in a protein that is unable to bind epidermal growth factor (EGF) but can still phosphorylate other substrates[14-15].

A variety of genetic alterations can occur in viral erb B oncogenes, e g amino acid substitutions and deletions in the carboxy terminus of the gene, wherein, the amino-terminal deletion is critical to carcinogenesis Amino-terminal deletions are a feature of all v-erb B oncogenes, including those that arise by promoter insertion or retroviral transduction[13, 16]. In contrast, carboxy-terminal deletions appear to be associated only with tumors that arise through retroviral transduction and seem to depend on host range and tumor type specificity[11, 15]. Transfection experiments with amino-terminal deleted avian c-erb B genes or viral oncogene-human EGF receptors demonstrate that this deletion is sufficient alone to create cell transformation[16-17].

Amplification of the EGFR gene occurs in 40% of the malignant human gliomas. Rearrangement of the receptor gene is evident in many of the tumors with gene amplification[3,7]. The rearrangements seem to preferentially affect the amino terminal of the gene[6, 18].

There are eight major variants of EGFR that are known: 1) EGFRvI lacks a majority of the extracellular domain of EGFR. 2) EGFRvII consists of an 83 aa in-frame deletion in the extracellular domain of EGFR. 3) EGFRvIII consists of a 267 aa in-frame deletion in the extracellular domain of EGFR. 4) EGFRvIV contains deletions in the cytoplasmic domain of EGFR. 5) EGFRvV contains deletions in the cytoplasmic domain of EGFR. 6) EGFR.TDM/2-7 contains a duplication of exons 2-7 in the extracellular domain of EGFR. 7) EGFR.TDM/18-26 contains a duplication of exons 18-26 in the extracellular domain of EGFR. 8) In addition, there is a second, rarer, EGFRvIII mutant (EGFRvIII/Δ12-13) that possesses a second deletion that introduces a novel histidine at the junction of exons 11 and 14[24].

EGFRvIII is the most commonly occurring variant of the epidermal growth factor (EGF) receptor in human cancers[24]. During the process of gene amplification, a 267 amino acid deletion occurs in the extracellular domain creating a novel junction (glycine). EGFRvIII is not known to be expressed on any normal tissues[19, 20]. (However, EGFRvIII shows significant expression in many tumor cells, e.g., through biopsies, it is demonstrated that 27~76% breast cancer express EGFRvIII[23], 50~70% gliomas express EGFRvIII[19, 22], 16% NSCL cancers express EGFRvIII[23], and 75% ovarian cancers express EGFRvIII[22]. Addtionally, the lab of the inventors has disclosed the presence of EGFRvIII in liver cancer.

However, up to now, people has not deeply understand the rational and mechanism underlying cancer invasion and metastasis. Therefore, it is urgent to discover proteins related to cancer invasion and metastasis in this field.

SUMMARY OF THE INVENTION

One purpose of the invention is to provide a novel polypeptide EGFRvA, which is associated to cancer invasion and metastasis, and the fragments, analogs as well as derivatives thereof.

Another purpose of the invention is to provide a polynucleotide encoding said polypeptides.

Still another purpose of the invention is to provide a method for preparing said polypeptides and the uses of said polypeptides and the encoding sequences thereof.

In the first aspect, the invention provides an isolated EGFRvA polypeptide, which includes a polypeptide having the amino acid sequence of SEQ ID NO: 2, the conservative variants, active fragments, and active derivatives thereof.

Preferably, said polypeptide is selected from the following groups:

(a) polypeptide having the amino acid sequence of SEQ ID NO: 2.

(b) polypeptide having the function to promote tumor cell invasion and/or increase tumor cell migration and derived from the polypeptide of (a) by substitution, deletion or addition of one or more (preferably, 1-10) amino acid residues in the amino acid sequence of SEQ ID NO:2.

(c) polypeptide derived from (a) and having at least 95% homology to the amino acid sequence of SEQ ID NO: 2 and capacity to promote tumor invasion or migration.

More preferably, the amino acid sequence of the polypeptide is the same as that shown in SEQ ID NO: 2.

The EGFRvA variant has a deletion of 120 amino acids in the end of the intracellular region of EGFR, and has a amino acid sequence consisting of 46 amino acid residuals shown as 1091-1136 of SEQ ID NO: 2 added at the end.

In the second aspect, the invention provides an isolated polynucleotide, which comprises a nucleotide sequence sharing at least 80% identity (preferably at least 90%, more preferably at least 95%) to the following nucleotide sequence: (a) the nucleotide sequence encoding the above EGFRvA polypeptide; (b) the polynucleotide complementary to nucleotide sequence of (a). Preferably; said nucleotide sequence encodes a polypeptide comprising the amino acid sequence of SEQ ID NO: 2. More preferably, said polynucleotide is selected from: (a) sequence containing residues from 44-3454 in the SEQ ID NO: 1; (b) sequence containing residues from 1-3763 in the SEQ ID NO: 1.

In the third aspect, the invention provides a vector comprising the above polynucleotide, and a host cell transformed or transducted with said vector or a host cell transformed or transducted with said polynucleotide.

In the fourth aspect, the invention provides a method for producing a polypeptide having the activity of human EGFRvA protein, which comprises: (a) culturing the above transformed or transducted host cell under the conditions suitable for the expression of the human EGFRvA protein; (b) isolating the polypeptides having the activity of human EGFRvA protein from the culture.

In the fifth aspect, the invention provides an antibody specifically binding the human EGFRvA protein.

In the sixth aspect, the invention provides compounds that can mimick, stimulate or antagonise the activity of the human EGFRvA polypeptide as well as compounds that can inhibit the expression of the human EGFRvA polypeptide. The invention also provides methods for screening and/or preparing these compounds. More preferably, the compound is the antisense sequence against the endocoding sequence for human EGFRvA polypeptide or the fragments thereof In the seventh aspect, the invention provides a method for detecting (especially non-diagnostically in vitro) the presence of EGFRvA protein, which comprises: incubating the sample with antibody specifically against EGFRvA protein; observing the formation of antibody complex; if there are antibody complex, it means the presence of EGFRvA protein.

In the eighth aspect, the invention provides a method for detecting diseases related to the abnormal expression of human EGFRvA polypeptide or susceptibility to the diseases, comprising the detection the mutation in the nucleotide sequence encoding said polypeptide.

In the ninth aspect, the invention provides the uses of the polypeptide according to the invention and the encoding sequence thereof For instance, the polypeptide of the invention can be used to select agonists or antagotists of the human EGFRvA polyptide activity, or to identify peptide mass fingerprinting. The encoding sequence of the human EGFRvA protein or the fragments thereof of the invention can be used as primers for the PCR amplification, as probes in hybridization reaction, or to make gene chip or microarray.

In the tenth aspect, the invention provides a pharmaceutical composition, comprising a safe and efficient amount of antagonist of human EGFRvA polypeptide and pharmaceutically acceptable carriers. Said pharmaceutical composition can be used for the treatment of diseases, such as breast cancer, glioma.

In another preferred example, said antagonists are antibodies that specifically bind to EGFRvA polypeptide but not human EGFR.

In the eleventh aspect, the invention provides a method for determinating whether the compound to be tested is antagonist or agonist of EGFRvA polypeptide, characterized in that, the method comprises the following steps:

(a) setting the test group by adding the compound to be tested into the culture of the tumor cells cultured in vitro; and setting the same tumor cells cultured in vitro as the control group, wherein, said tumor cells are from mammalian and express the EGFRvA polypeptide of the invention;

(b) observing the migration of the tumor cells in the test group and the control group, and if the migration of the tumor cells in the test group is greater than that of the control group, it indicates that the compound tested is the agonist of the EGFRvA polypeptide, and if the migration of the tumor cells in the test group is less than that of the control group, it indicates that the compound tested is the antagonist of EGFRvA polypeptide.

In another preferred example, said tumor cells are human tumor cells.

The other aspects of the invention will be apparent to the skilled in the art in light of the technical disclosure of the invention.

DESCRIPTION OF THE FIGURES

The following drawings are used to elucidate the specific examples of the present invention, not to limit the scope of the invention as defined by the claims.

DETAILED DESCRIPTION OF INVENTION

Figure 1:
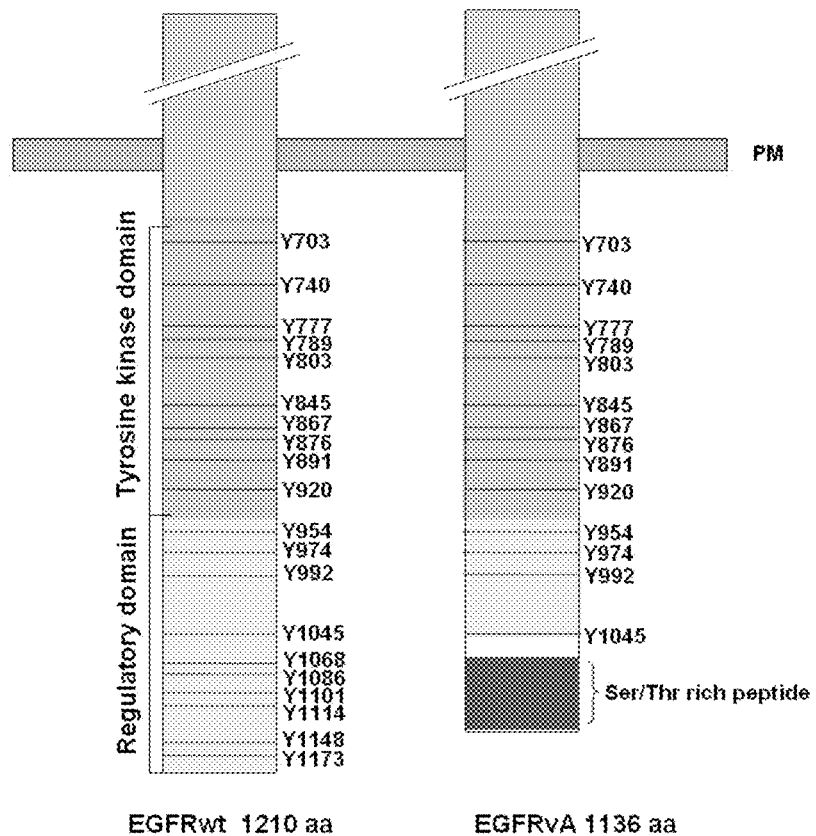
FIG. 1 shows the difference between EGFRvA and EGFR.

After extensive and in-depth research, the present inventors first found and isolated a novel EGFR variant (EGFRvA) which has the following characteristics: 1) it has a deletion of 120 amino acids at the end of the intracellular region of the epidermal growth factor receptor, and has a amino acid sequence consisting of 46 amino acid residuals shown as 1091-1136 of SEQ ID NO: 2 added at the end. 2) it exists in a variety of normal tissues and tumor tissues, and is overexpressed in certain tumor tissues. 3) It can significantly promote tumor cell invasion and migration in vitro. 4) It can significantly promote tumor cell metastasis in vivo. 5) compared with wild-type EGFR (EGFRwt), it has lower sensitivity to small molecule kinase inhibitors. 6) RNA interference against it can lead to the death of certain cells. 7) It also has some mutations in exon No. 19 or No. 21 in some lung cancer patients. On this basis, the present invention was finished.

Moreover, the present inventors also developed methods for detecting this gene: 1) RT-PCR was used to detect the gene and the mutation in exon 19 and 21 of the gene. 2) Monoclonal antibodies were screened to detect the protein levels for EGFRvA and EGFRwt. 3) shRNA specific for EGFRvA was also made.

In the present invention, the term "EGFRvA protein", "EGFRvA polypeptide" or "Epidermal Growth factor receptor variant EGFRvA" can be used interchangeably, all referring to the human epidermal growth factor receptor variant EGFRvA protein or polypeptide comprising amino acid sequence (SEQ ID NO: 2). They include the epidermal growth factor receptor variant EGFRvA with or without the initiation methionine.

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been separated from other components naturally accompanying them, they are isolated or purified.

As used herein, the term "isolated EGFRvA protein or polypeptide" means that EGFRvA polypeptide does not essentially contain other proteins, lipids, carbohydrate or any other substances associated therewith in nature. The skilled in the art can purify EGFRvA protein by standard protein purification techniques. Essentially purified polypeptide forms a single main band on a non-reductive PAGE gel. The purity of EGFRvA polypeptide can be analyzed by amino acid sequence analysis.

The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacteria, yeast, higher plant, insect, and mammalian cells, using recombination techniques. According to the host used in the protocol of recombination production, the polypeptide of the invention may be glycosylated or non-glycosylated. The polypeptide of the invention may or may not comprise the starting Met residue.

The invention further comprises the fragments, derivatives and analogues of EGFRvA. As used herein, the terms "fragment", "derivative" and "analogue" mean the polypeptide that essentially retains the same biological functions or activity of EGFRvA protein of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which the mature polypeptide is fused with another compound, such as a compound to increase the half-life of the polypeptide (for example, polyethylene glycol), or (iv) one in which the additional amino acid sequence is fused to the polypeptide, such as a leader or secretary sequence or a sequence which is employed for purification of the polypeptide or a proprotein sequence, or a fusion protein formed with IgC fragment. Such fragments, derivatives and analogs are deemed to be within the scope of those skilled in the art from the teachings herein.

In the present invention, the term "human EGFRvA polypeptide" refers to a polypeptide having the activity of human EGFRvA protein comprising the amino acid sequence of SEQ ID NO: 2. The term also includes the variants of said amino acid sequence which have the same function as human EGFRvA. These variants include, but are not limited to, deletions, insertions and/or substitutions of one or more amino acids (typically 1-50, preferably 1-30, more preferably 1-20, most preferably 1-10), and addition of one or more amino acids (typically less than 20, preferably less than 10, more preferably less than 5) at C-terminal and/or N-terminal For example, the protein functions are usually unchanged when an amino residue is substituted by a similar or analogous one. Further, the addition of one or several amino acids at C-terminal and/or N-terminal will not change the function of protein. The term also includes the active fragments, and derivatives of EGFRvA protein.

The variants of the polypeptide include homologous sequences, conservative variants, allelic variants, natural mutants, induced mutants, proteins encoded by DNA which hybridizes to human EGFRvA DNA under high or low stringency conditions as well as the polypeptides or proteins obtained using antisera raised against human EGFRvA polypeptide. The present invention also provides other polypeptides, e.g., fusion proteins comprising human EGFRvA polypeptide or fragments thereof (for example, the fusion protein of SEQ ID NO: 3). In addition to the substantially full-length polypeptide, the soluble fragments of human EGFRvA polypeptide are also included. Generally, these fragments comprise at least 10, typically at least 30, preferably at least 50, more preferably at least 80, most preferably at least 100 consecutive amino acids of human EGFRvA polypeptide.

The present invention also provides the analogues of human EGFRvA protein or polypeptide. The analogues can differ from naturally occurring human EGFRvA polypeptide in amino acid sequence or modifications which do not affect the sequence, or both. These polypeptides include naturally or induced genetic variants. Induced variants can be obtained by various techniques, e.g., by random mutagenesis using irradiation or exposure to mutagens, or by site-directed mutagenesis or other known molecular biologic techniques. Also included are analogues which comprise residues other than those naturally occurring L-amino acids (e.g., D-amino acids) or non-naturally occurring or synthetic amino acids (e.g., beta- or gamma-amino acids). It should be understood that the polypeptides of the invention are not limited to the representative polypeptides listed hereinabove.

Modifications (which do not normally alter primary sequence) include: in vivo or in vitro chemical derivation of polypeptides, e.g., acelylation, or carboxylation. Also included are modifications of glycosylation, e.g., those polypeptides made by glycosylation during the synthesis and processing or in the further processing steps of the polypeptides. Said modification can be achieved by exposing the polypeptide to enzymes for glycosylation (e.g., mammalian glycosylating or deglycosylating enzymes). Also included are sequences which have phosphorylated amino acid residues, e.g., phosphotyrosine, phosphoserine, phosphothronine, as well as the polypeptides which have been modified to improve the resistance to proteolytic degradation or to optimize solubility properties.

In the invention, "human EGFRvA conservative mutant polypeptide" means a polypeptide formed by substituting at most 10, preferably at most 8, more preferably 5, and most preferably at most 3 amino acids with the amino acids having substantially the same or similar property, as compared with the amino acid sequence of SEQ ID NO: 2. Preferably, these conservative mutants are formed by the amino acids substitution according to Table 1.

TABLE 1

| The initial residues | Representative substitutions | Preferred substitutions |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The polynucleotide according to the invention may be in the form of DNA or RNA. DNA includes cDNA, genomic DNA, and artificially synthesized DNA, etc., in single strand or double strand form. A DNA may be an encoding strand or non-encoding strand. The coding sequence for mature polypeptide may be identical to the coding sequence shown in SEQ ID NO: 1, or is a degenerate sequence. As used herein, the term "degenerate sequence" means the nucleotide sequence which encodes a protein or peptide comprising a sequence of SEQ ID NO: 2, but is different from the sequence of coding region in SEQ ID NO: 1.

The polynucleotide encoding the mature polypeptide of SEQ ID NO: 2 includes: the encoding sequence merely encoding the mature polypeptide, the encoding sequence encoding mature polypeptide plus various additional encoding sequence, the encoding sequence for mature polypeptide plus the non-encoding sequence and optional additional encoding sequence.

The term "polynucleotide encoding the polypeptide" includes the polynucleotide encoding said polypeptide and the polynucleotide further comprising additional and/or non-encoding sequence.

The invention further relates to the variants of the hereinabove polynucleotides which encode a polypeptide having the same amino acid sequence of invention, or the fragment, analogue and derivative thereof. The variant of the polynucleotide may be a naturally occurring allelic variant or a non-naturally occurring variant . Such nucleotide variants include substitution, deletion, and insertion variants. As known in the art, the allelic variant is a substitution form of polynucleotide, which may be a substitution, deletion, and insertion of one or more nucleotides without substantially changing the functions of the encoded polypeptide.

The present invention further relates to a polynucleotide, which hybridizes to the sequences said above, and there is at least 50%, preferably at least 70%, more preferably at least 80% identity between the two sequences. The present invention particularly relates to the polynucleotides, which hybridize under stringent conditions to the polynucleotides of the invention. As herein used, the term "stringent conditions" means the following conditions: (1) hybridization and washing are conducted under low ionic strength and high temperature, such as 0.2×SSC, 0.1% SDS, 60° C.; (2) hybridization is conducted with denaturants added, such as 50% (v/v) formamide, 0.1% bovine serum/0.1% Ficoll, 42° C.; or (3) hybridization occurs merely under the condition that the two sequences sharing at least 95%, preferably 97% identity. Further, the polypeptide encoded by the polynucleotides which hybridize to the polynucleotides said above pocesses the same biological function or activity as the mature polypeptide as set forth in SEQ ID NO: 2.

The invention also relates to nucleic acid fragments which can hybridize with the sequence said above. As used herein, the length of the "nucleic acid fragment" is at least 15 bp, preferably at least 30 bp, more preferably at least 50 bp, and most preferably at least 100 bp. The nucleic acid fragment can be used in the amplification techniques of nucleic acid, e.g., PCR, so as to determine and/or isolate the polynucleotide encoding EGFRvA.

The polypeptide and polynucleotide of the invention are preferably in isolated form, preferably purified to homogenous.

The full-length sequence or the fragments thereof of the human EGFRvA according to the invention can be obtained by PCR amplication, recombination or artificial synthesis. For PCR amplification, the primers can be designed according to the nucleotide sequences disclosed in the invention, especially the sequence of open reading frame, and the commercially available cDNA library or the cDNA library prepared using the routine methods known by the skilled person can be used as the templates, thereby amplifying the relevant sequences. If the sequence to be amplified is long, the PCR can be conducted for two or more times, and then the amplified fragments can be connected together in the correct order.

Once the sequence is obtained, huge number of the sequence can be produced by combination. Generally, the sequence can be cloned into a vector, and then the vector can be transferred into the cells. The related sequences can be isolated from the amplified host cells by conventional methods.

Furthermore, the related sequence, especially shorter fragment can also be synthesized by artificiall synthesis. Generally, a number of small fragments are firstly synthesized, and then connected together to obtain long sequence fragment.

Now the DNA sequence encoding the protein of the invention (or the fragment or derivative thereof) can be completely obtained by chemical synthesis. The DNA sequence may then be introduced into the various DNA molecules (or vectors) and cells known in the art. In addition, mutations also can be introduced into the protein sequence of the present invention by chemical synthesis.

Methods that amplify DNA/RNA using PCR technique (Saiki, et al. Science 1985; 230:1350-1354) are preferably used for obtaining the gene of the invention. Especially when full-length cDNA can not be readily obtained from the library, RACE method (rapid amplification of the end of the RACE-cDNA) can be preferably used. Primers used in PCR may be appropriately selected based on the sequence information disclosed in the present invention, and can be synthesized by a conventional method. The amplified DNA/RNA fragment can be separated and purified by conventional methods such as gel electrophoresis.

The present invention also relates to a vector containing the polynucleotide of the present invention and a host cell produced by genetic engineering using the vectors of the invention or coding sequence of EGFRvA protein, as well as methods to produce said polypeptide in the present invention by the recombination techniques.

The recombinant EGFRvA polypeptides can be expressed or produced by the conventional recombination DNA technology (Science, 1984; 224:1431), using the polynucleotide sequence of invention. Generally, it comprises the following steps:

(1) Transforming or transducing suitable host cells using the polynucleotide according to the invention encoding the human EGFRvA polypeptide (or the variants thereof),or using the recombination expression vector comprising the polynucleotide;

(2) culturing the host cells in an appropriate medium;

(3) isolating or purifying the protein from the medium or cells.

In the present invention, the polynucleotide sequences encoding human EGFRvA may be inserted into a recombination expression vector. The term "recombination expression vector" refers to a bacterial plasmid, bacteriophage, yeast plasmid, plant virus or mammalian cell virus, such as adenovirus, retrovirus or any other vector known in the art. Vectors suitable for the present invention include, but are not limited to, the T7-based expression vector for expression in bacteria (Rosenberg, et al., Gene, 56:125, 1987), the pMSXND expression vector for expression in mammalian cells (Lee and Nathans, J Biol. Chem., 263:3521, 1988) and baculovirus-derived vectors for expression in insect cells. Any plasmid or vector can be used, as long as it can replicate and is stable in the host. One important feature for a expression vector is that the expression vector typically contains an origin of replication, a promoter, a marker gene as well as the translation regulatory elements.

The methods known by the artisans in the art can be used to construct an expression vector containing the DNA sequence encoding human EGFRvA and appropriate transcription/translation regulatory elements. These methods include in vitro recombination DNA technique, DNA synthesis technique, in vivo recombination technique and so on (Sambrook, et al. Molecular Cloning, a Laboratory Manual, Cold Spring Harbor Laboratory. New York, 1989). The DNA sequence is efficiently linked to the proper promoter in the expression vector to direct the synthesis of mRNA. The exemplary promoters are lac or trp promoter of E. coli; $P_L$ promoter of 2, phage; eukaryotic promoter including CMV immediate early promoter, HSV thymidine kinase promoter, early and late SV40 promoter, LTRs of retrovirus and some other known promoters which can control the gene expression in the prokaryotic cells, eukaryotic cells or virus. The expression vector may further comprise a ribosome-binding site for initiating the translation, transcription terminator and the like.

Furthermore, the expression vector preferably comprises one or more selective marker genes to provide a phenotype for selecting the transformed host cells, e.g., the dehydrofolate reductase, neomycin resistance gene and GFP (green flurencent protein) for eukaryotic cells, as well as tetracycline or ampicillin resistance gene for E. coli.

The vector containing proper DNA sequence said above and proper promoter or regulatory sequences can be transformed into appropriate host cells to express the protein.

The "host cell" includes prokaryote, such as bacteria; primary eukaryote, such as yeast; advanced eukaryotic, such as mammalian cells. The representative examples are bacterial cells, such as E. coli, Streptomyces, Salmonella typhimurium; fungal cells, such as yeast; plant cells; insect cells such as Drosophila S2 or Sf9; animal cells such as CHO, COS, 293 cells or Bowes melanoma cells, etc.

When expressed in advanced eukaryotes, the transcription of the polynucleotide of the invention can be increased by inserting an enhancer sequence into the vector. Enhancers are cis-acting elements of DNA, usually about from 10 to 300 bp, which act on a promoter to enhance the gene transcription. Examples include the SV40 enhancer on the late side of the replication origin 100 to 270 bp, the polyoma enhancer on the late side of the replication origin, and adenovirus enhancers, etc.

The skilled person in the art know clearly how to select appropriate vectors, promoters, enhancers and host cells.

Transformation of host cell with the recombination DNA can be carried out by conventional techniques well known to those skilled in the art. When the host is prokaryotic such as E. coli, the competent cells, which are capable of uptaking DNA, can be harvested after exponential growth phase, and then treated by the $CaCl_2$ method using procedures well known in the art. Alternatively, $MgCl_2$ can be used. The transformation can also be carried out by electroporation, if necessary. When the host is an eukaryote, the following methods of DNA transfection can be selected: calcium phosphate co-precipitates, conventional mechanical procedures such as micro-injection, electroporation, or liposome-mediated transfection, etc.

The obtained transformants can be cultured using conventional methods to express the polypeptides encoded by the genes of the invention. According to the used host cells, the medium for cultivation can be selected from various conventional mediums. The host cells are cultured under a condition suitable for its growth until an appropriate cell density is obtained. Then, the selected promoter is induced by appropriate means (e.g., temperature shift or chemical induction) and cells are cultured for an additional period.

In the above methods, the recombinant polypeptide may be expressed in the cells, or on the cell membrane, or secreted out of the cell. If necessary, the recombinant protein can be isolated or purified by various isolation methods through the physical, chemical and other properties of the protein. These methods are well-known to those skilled in the art and include, but are not limited to: conventional renaturation treatment, treatment by protein precipitant (such as salting out), centrifugation, cell lysis by osmosis, sonication, supercentrifugation, molecular sieve chromatography or gel chromatography, adsorption chromatography, ion exchange chromatagraphy, HPLC, and any other liquid chromatagraphy, and the combinations thereof.

The recombinant human EGFRvA protein or polypeptide have various uses including, but not to be limited to: used as medicaments for treating diseases due to the lower or no activity of EGFRvA protein, and screening antibodies, polypeptides or other ligands as agonists or antagonists of EGFRvA. The expressed recombinant human EGFRvA protein can be used to screen polypeptide library for therapeutically valuable polypeptide molecules which can inhibit or activate human EGFRvA protein.

In another aspect, the invention also includes polyclonal antibodies and monoclonal antibodies specifically against the polypeptides encoded by human EGFRvA DNA or the fragments thereof, especially monoclonal antibodies. Here, "specifically" means that the antibody can bind to the product or the fragments thereof of human EGFRvA gene. More preferably, the antibodies can bind to the product or the fragments thereof of human EGFRvA gene but can not recognize and bind to non-relevant antigens. The antibodies of the invention include molecules that can bind to and inhibit human EGFRvA protein as well as antibodies that do not affect the function of human EGFRvA protein. The invention also includes the antibodies that can bind to modified or unmodified product of human EGFRvA gene.

The invention not only includes whole monoclonal or polyclonal antibodies but also antibody fragments possessing immune activities such as Fab', $(Fab)_2$, heavy chain of antibody, light chain of antibody, single-chain Fv molecules modified by genetic engineering (Ladner et al, U.S. Pat. No. 4,946,778) or chimeric antibodies, such as antibodies that possesses the binding specificities of the mouse antibodies while remaining part of human antibodies.

The antibodies of this invention can be prepared by techniques known by technicians in this field. For example, the purified human EGFRvA gene product or the antigenic fragments thereof can be administered to the animal to induce polyclonal antibody. Similarly, cells expressing human EGFRvA protein or the antigenic fragments thereof can be used to immunize animals to produce antibodies. The antibodies of the present invention can also be monoclonal antibodies. Such monoclonal antibodies can be prepared by hybridoma technology (see Kohler et al, Nature, 256; 495, 1975; Kohler, et al, Eur.J.Immunol 6:511,1976; Kohler, etc. Eur.J.Immunol 6:292,1976; Hammerling et al, In Monoclonal Antibodies and T the Cell Hybridomas, Elsevier, N.Y., 1981). The antibodies of this invention include the antibody that can block the function of human EGFRvA protein or do not affect the function of human EGFRvA protein. Various types of antibodies of the present invention can be obtained through the routine immunization technology using fragments or functional domains of human EGFRvA gene product. These fragments or functional domains can be prepared by recombination method or synthesized using polypeptide synthesizer. The antibodies binding the unmodified human EGFRvA gene product can be produced by immunizing animals using gene products produced in prokaryotic cells (eg $E.$ $Coli$); antibodies binding the post-translational modified human EGFRvA gene product (such as glycosylated or phosphorylated proteins or peptides) can be obtained by immunizing animals using gene products produced in eukaryotic cells (eg, yeast or insect cells).

Anti-human EGFRvA protein antibodies can be used in immunohistochemical techniques for detecting biopsy specimens for EGFRvA protein.

The antibodies of this invention can be used for the treatment or prevention of disease related to human EGFRvA protein. An appropriate dose of the antibody can be administrated to stimulate or block the production or activity of the human EGFRvA protein.

The antibody can also be designed as an immunotoxin targeting to a special part of the body. For example, high-affinity monoclonal antibody against human EGFRvA protein can be covalently conjugated with the bacterial or plant toxins (such as diphtheria toxin, ricin, abrin, etc.). Generally, thiol crosslinkers such as SPDP is used to attack the amino-group of antibodies, thereby conjugating the toxin to the antibodies through disulfide exchange. The hybrid antibody can be used to kill the human EGFRvA protein-positive cells.

The polyclonal antibodies can be made by immunizing animals, such as rabbits, mice, rats, and so on using the human EGFRvA protein or polypeptide. A variety of adjuvants, including but not limited to Freund's adjuvant, can be used to enhance the immune response.

Using the protein of the invention, the substances interacted with EGFRvA protein, such as receptors, inhibitors, agonists or antagonists and be screened out through a variety of conventional screening methods.

When applied (administered) therapeutically, the protein according to the invention and the antibody, inhibitor, agonist, antagonist or receptor thereof can produce different effects. Generally, these substances can be formulated in a non-toxic, inert and pharmaceutically acceptable aqueous carrier medium, wherein pH is usually around 5-8, preferably, 6-8, although the pH value can be changed according to the nature of the formulated substances and the disease to be treated. The prepared pharmaceutical compositions can be administered by conventional routes, including (but not limited to): intramuscular, intraperitoneal, intravenous, subcutaneous, intradermal, or topical administration.

Antibodies against the EGFRvA protein of the present invention can be used to treat diseases, for example, to inhibit tumor cell invasion or migration. Antibodies of the present invention can also be used in combination with other therapeutic agents, such as anti-tumor chemotherapy agents.

The present invention also provides a pharmaceutical composition, which contains the safe and effective amount of EGFRvA polypeptide or the agonist, antagonist thereof according to the invention and a pharmaceutically acceptable carrier or excipient. Such vectors include (but are not limited to): saline, buffers, glucose, water, glycerol, ethanol, and combinations thereof. Pharmaceutical formulation should match the mode of administration. The pharmaceutical compositions of this invention can be prepared as injection form, for instance, using normal saline or aqueous solution containing glucose and other auxiliary agents by conventional methods. Pharmaceutical compositions such as tablets and capsules can be prepared by conventional methods. Pharmaceutical compositions, such as injection solutions, solutions, tablets and capsules should be manufactured under sterile conditions. The dosage of the active ingredient is a therapeutically effective amount, such as about 1 µg/kg body weight-5 mg/kg body weight per day. In addition, the polypeptide of the present invention can also be used in combination with other therapeutic agents.

The pharmaceutical compositions with a safe and effective dose of EGFRvA protein or the antagonist, agonist thereof shall be applied to mammals, wherein the safe and effective amount is usually at least about 10 micrograms/kg body weight, and in most cases no more than about 8 mg/kg body weight, preferably, about 10 micrograms/kg body weight-1 mg/kg body weight. Of course, for the specific dose, factors such as the route of administration, patient health status should also be considered, which are in the range of skills for the skillful physician.

The polynucleotide of human EGFRvA protein can be used for a variety of therapeutic purposes. Gene therapy can be used to treat cel proliferation, developmental or metabolic abnormalities caused by non-expression of EGFRvA protein or abnormal/inactive expression of EGFRvA protein. The recombinant gene therapy vector (such as viral vectors) can be designed for expressing the EGFRvA protein variants to suppress the endogenous EGFRvA protein activity. Expression vectors derived from viruses such as retrovirus, adenovirus, adeno-associated virus, herpes simplex virus, parvovirus can be used to transfer EGFRvA gene into cells. Methods for constructing recombinant viral vectors carrying the EGFRvA gene can be found in the literature (Sambrook et al.). Additionally, recombinant human EGFRvA gene can be packed into liposomes, and then transferred into the cells.

Oligonucleotides (including antisense RNA and DNA) as well as the ribozyme that can inhibit the human EGFRvA mRNA is also fall within the scope of the present invention. Ribozyme is an enzyme-like RNA molecule that can specifically break down target RNAs. The underlying mechanism is the endonuclease cleavage upon specific hybridization of the ribozyme molecule with the complementary target RNA. Antisense RNA and DNA, as well as ribozymes can be obtained by any available RNA or DNA synthesis method, such as phosphoric acid amide chemical synthesis in solid phase synthesis of oligonucleotide technology which has been widely applied. Antisense RNA molecules can be prepared by in vitro or in vivo transcription of the DNA sequence encoding the RNA. Such DNA sequence is integrated into the downstream of RNA polymerase promoter in the vectors. For increasing the stability of the nucleic acid molecules, the molecules can be modified by many methods, such as increasing the length of the sequence at both sides. Ribonucleosides should be connected by ribonucleoside thioester bond or peptide bond instead of the phosphodiester bond.

The methods for introducing the polynucleotide into tissues or cells include: directly injecting the polynucleotide into the body tissues; or introducing the polynucleotide into the cells by a vector (such as virus, phage or plasmid) and then transplanting the cells into the body.

Polypeptides that can bind to human EGFRvA protein can be obtained by screening random polypeptide libraries composed of a variety of possible combinations of amino acids bound to the solid phase. The human EGFRvA protein should be labeled for screening.

The invention also relates to diagnostic test methods for quantitative and locative detection of human EGFRvA protein level. These tests including FISH determination and radioimmunoassay are well known in this field. The level of the human EGFRvA protein can be used to explain the importance of human EGFRvA protein in various diseases and diagnose diseases wherein EGFRvA proteins play a role.

A detection method for testing the presence of EGFRvA protein in the samples uses antibodies specific for EGFRvA proteins. It comprises: contacting the sample with antiboides specific for EGFRvA proteins; and observing the formation of the antibody complex; if antibody complexes form, it indicate the presence of EGFRvA protein in the sample.

The polynucleotide of EGFRvA protein can be used for the diagnosis and treatment of EGFRvA protein-related diseases. For the diagnosis, polynucleotide of EGFRvA protein can be used to detect the expression of EGFRvA protein or the abnormal expression of EGFRvA protein in disease states. For instance, the EGFRvA DNA sequences can be used to hybridize with biopsy specimens and determine the abnormalities of EGFRvA protein expression. Hybridization includes Southern blotting, Northern blotting and in situ hybridization. These techniques are known technology, and the relevant kits can be obtained from the commercial routes. Part or all of the polynucleotide of the present invention can be used as a probe in the microarray or DNA chips (also referred to as "gene chips") to analyze the differential gene expression in tissues and gene diagnosis. In vitro amplification by RNA-polymerase chain reaction (RT-PCR) using the EGFRvA protein specific primers can also be applied to detect transcripts of EGFRvA protein.

EGFRvA protein-related diseases can be disgnosed by detecting mutations in EGFRvA gene. Compared with the normal wild-type EGFRvA DNA sequences, the mutation of EGFRvA protein includes point mutation, translocation, deletion, recombination and any other abnormalities. Available technology, such as Southern blotting, DNA sequencing, PCR and in situ hybridization can be used to detect the mutations. In addition, the mutation may affect protein expression. Therefore, Northern blotting, Western blotting can be used to indirectly determine whether the gene possesses mutations or not.

The sequence of this invention is also valuable for chromosome identification. In short, the sequence of PCR primers (preferably 15-35 bp) prepared according to cDNA encoding EGFRvA protein in the present invention can be located on chromosomes. Then, these primers can be used in PCR screening of somatic heterozygous cells containing human chromosomes. Only those heterozygous cells containing the human genes corresponding to the primers can produce amplified fragments.

Once the sequence is positioned to the exact chromosomal location, the physical location of this sequence on the chromosome can be associated with genetic map data. These data can be found in, for example, V.Mckusick Mendelian Inheritance in Man, (available through Johns Hopkins University Welch Medical Library Online). And then linkage analysis can be used to determine the relationship between genes and disease that has been localized to chromosomal regions.

In an example of the present invention, a separated polynucleotide is provided, which encodes polypeptide comprising the amino acid sequence of SEQ ID NO: 2. Its sequence is shown in SEQ ID NO: 1 which contains 3763 by in full-length, with open reading frame located in 44-3454, and encoding the human EGFRvA protein comprising 1136 amino acids in full-length (SEQ ID NO: 2).

The present invention will be further illustrated below with reference to specific examples. It should be understood that these examples are not to limit the scope of the present invention, rather to illustrate it. The experimental methods with no specific conditions described in the following examples are generally performed under conventional conditions, such as those described in Sambrook et al. Molecular Cloning: A Laboratory Manual (New York: Cold Spring Harbor Laboratory Press, 1989), or according to manufacturers' instructions.

EXAMPLE 1

Obtaining EGFRvA sequence by PCR

Materials and methods: Normal tissue RNA samples were purchased from Clontech. The tissues involved are: brain (catalog No. 636530), colon (catalog No. 636553), kidney (catalog no. 636529), liver (catalog no. 636531), lung (catalog no. 636524), ovary (catalog no 636555), pancreas (catalog no. 636577), placenta (catalog no. 636527), spleen (catalog no. 636525), stomach (catalog no. 636578), prostate (catalog no. 636550), breast (catalog no. 636576). The nested-PCR was used to amplify the above samples.

|  | Sequence | SEQ ID NO: |
|---|---|---|
| Amplification of short strand | | |
| Forward primer of first-round | 5'-TCCCCTCCTGAGCTCTCTGAG-3' | 3 |
| Reverse primer for EGFRwt in first-round | 5'-TGACTTGATACAGTACCGATCCGG-3' | 4 |

| Sequence | SEQ ID NO: |
|---|---|
| Reverse primer for EGFRvA in first-round     5'-TGTACACACATCATGAACACTCACACA-3' | 5 |
| Forward primer of second round     5'-AGTGCAACCAGCAACAATTCCA-3' | 6 |
| Reverse primer for EGFRwt in second-round     5'-GGAATCAAGCATCCTCTGGAAGAC-3' | 7 |
| Reverse primer for EGFRvA in second-round     5'-CAACAGAGGTACAGCAAACAACCAG-3' | 8 |
| Amplification of long strand | |
| Forward primer of first-round     5'-GTATTGATCGGGAGAGCCG-3' | 9 |
| Reverse primer for EGFRwt in first-round     5'-TGACTTGATACAGTACCGATCCGG-3' | 10 |
| Reverse primer for EGFRvA in first-round     5'-TGTACACACATCATGAACACTCACACA-3' | 11 |
| Forward primer of second round     5'-ATGCGACCCTCCGGGACG-3' | 12 |
| Reverse primer for EGFRwt in second-round     5'-GGAATCAAGCATCCTCTGGAAGAC-3' | 13 |
| Reverse primer for EGFRvA in second-round     5'-CAACAGAGGTACAGCAAACAACCAG-3' | 14 |

Figure 2A:
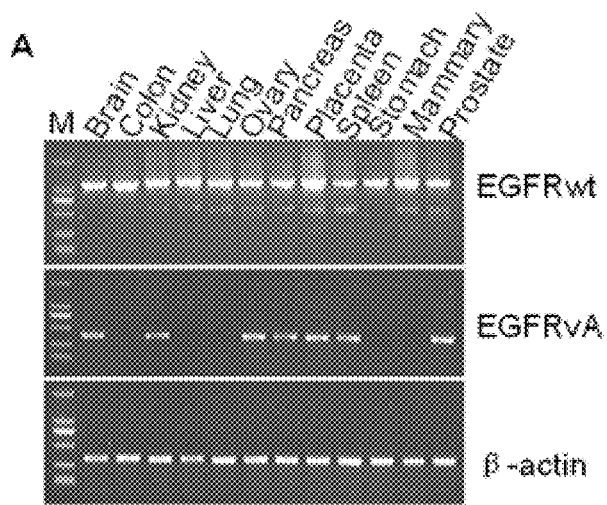
FIG. 2A shows the RNA expression level of EGFRvA in various normal tissues.

Results: EGFRwt can be amplified in all the tested tissues. However, in liver, lung, stomach, colon or breast, no obvious band can be observed in the amplification of EGFRvA. Besides, the full-length sequence of EGFRvA was obtained in the normal tissues of ovary and prostate (FIG. 2A).

EXAMPLE 2

Detecting mRNA Expression Levels of EGFRvA in Tumor Cells and Tissues

The following cell lines were used in this example: human epithelial carcinoma cell line A431 (ATCC, Manassas, Va., USA), human breast cancer cell line MDA-MB-468 (ATCC, Manassas, Va., USA), human glioblastoma-astrocytoma, epithelial-like cell line U87MG (ATCC, Manassas, Va., USA), human liver cancer cell line Bel-7402 (Chinese Academy of Science, Shanghai, China); human prostate cancer cell line PC-3 (ATCC, Manassas, Va., USA); human lung adenocarcinoma cell line H1299 (ATCC, Manassas, Va., USA); human ovarian cancer cell line SKOV-3 (ATCC, Manassas, Va., USA). The cells were cultured in DMEM medium (Gibco, Grand Island, N.Y.) supplemented with 10% fetal calf serum (PAA Laboratories) and antibiotics (Gibco, Grand Island, N.Y.). Lung cancer and paracancerous tissue used in the example were obtained from Shanghai Chest Hospital (NSCLC) along with written informed consent. Liver cancer and paracancerous tissue used in the example were obtained from Qidong Liver Cancer Institute (HCC) along with written informed consent. Such studies and the use of all clinical materials within this study have been approved by the related Institutional Ethics Review Committee.

Figure 2B:
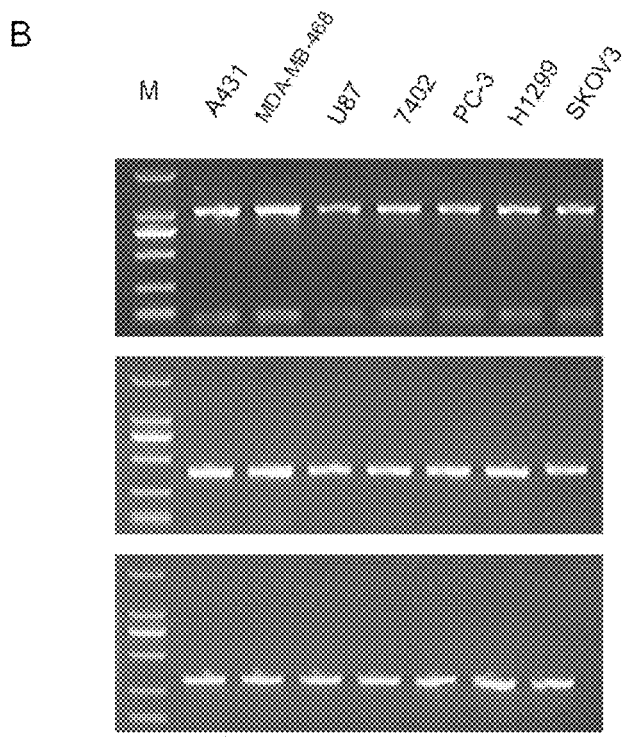
FIG. 2B shows the EGFR expression in tumor cell lines (RT-PCR)
Figure 2C:
FIG. 2C shows the EGFR expression in tumor cell lines (Western BlottingRT-PCR).
Figure 2D:
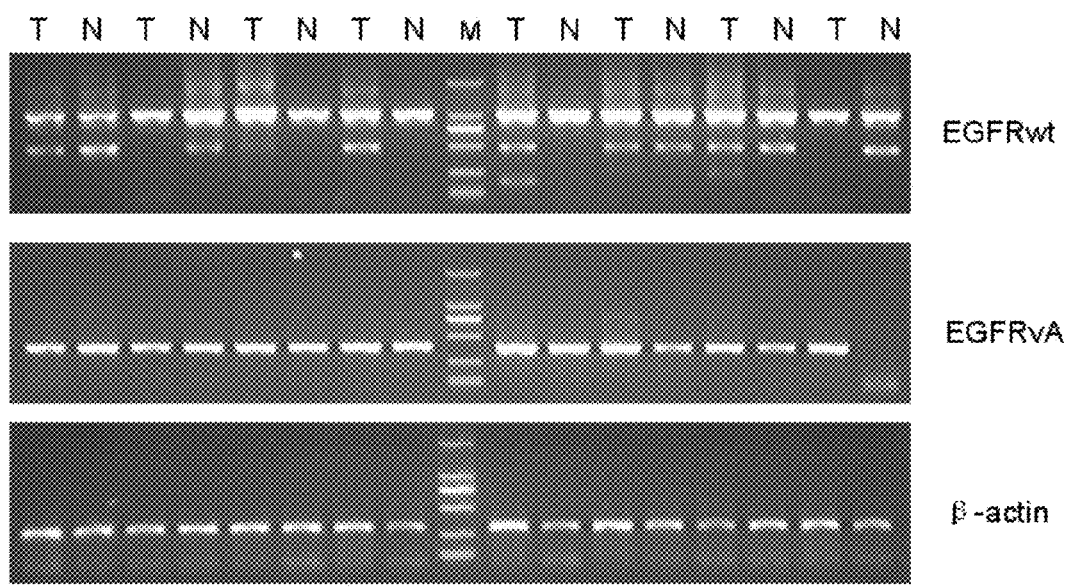
FIG. 2D shows the EGFRvA expression in lung tumor tissues. T represents tumor tissue while N represents tumor tissues.

Results: the expression of EGFRvA RNA was observed in almost all of the tumor cell lines and most of the cancer and paracancerous tissues (FIG. 2B and 2D).

EXAMPLE 3

Preparation of Monoclonal Antibodies Recognizing EGFRvA or EGFRwt

Polypeptide in the intracellular region of EGFRwt and EGFRvA were synthesized respectively. Then the polypeptides and ceruloplasmin (KLH) were cross-linked at 1:1 quality ratio. 100 ug of peptide-KLH was mixed with Freund's complete adjuvant at 1:1 quality ratio and used to immunize mice. Four weeks later, 100 μg of peptide-KLH was mixed with incomplete Freund adjuvant at 1:1 ratio and used to immunize mice. 2 weeks later, immunization was repeated once again. Monoclonal antibody was screened by conventional hybridoma technology and its specificity was determined using cell lines stably expressing EGFRwt and EGFRvA. These antibodies can be applied in the ELISA, Western Blot (WB), immunofluorescence (IF) and immunohistochemistry (IHC) for EGFRwt, and EGFRvA detection.

Results: monoclonal antibody 1F3-52 which can specifically recognizes EGFRvA and monoclonal antibody 1C5 which can specifically recognizes EGFRwt were obtained.

EXAMPLE 4

Detecting the Expression Level of EGFRvA Protein in the Tumor Cells and Tissues

The lysates from the tissues and cells were quantified using BCA kit (Pierce, Rockford, Ill.). 30 μg of proteins were separated on 10% SDS-PAGE gels and transferred to nitrocellulose membranes (Millipore Billerica). The membrane were then blocked with 5% skimmed milk and incubated overnight with primary antibody at 4° C. Mouse anti-GAPDH antibody was purchased from Shanghai Kangcheng Biotechnology, Inc(Shanghai, China). Rabbit anti-human EGFR antibody SC-03 was purchased from Santa Cruz Biotechnology, Inc. (CA). Monoclonal antibodies 1F3-52 which can specifically recognizes EGFRvA and 1C5 which can specifically recognize EGFRwt were prepared in-house. The immune complexes and goat anti-mouse antibody labled with horseradish peroxidase (Immu-Club Labs, Sunnyvale, Calif.) were incubated at room temperature for 1 hour and detected using a chemiluminescence reagent (Pierce, Rockford, Ill.)

Results: The expression of EGFRvA protein was observed in some tumor cell lines such as A431, MDA-MB-468 (FIG. 2C). The expression of EGFRvA protein was also observed in lung cancer tissues.

EXAMPLE 5

Preparation of Lentivirus and Establishment of Stable Cell Transfectants

EGFRwt and EGFRvA sequence were amplified from A431 cell line respectively. After sequenced, the DNA was inserted into pWPT vector (purchased from Addgene) to replace GFP, thereby producing the pWPT-EGFRwt and pWPT-EGFRvA. The pWPT-EGFRwt or pWPT-EGFRvA were co-transduced with packaging plasmid psPAX2 and G-protein of vesicular stomatitis virus (VSV-G) membrane plasmid pMD2.G (purchased from Addgene) into 293T cells (Chinese academy, Shanghai, China) using calcium phosphate. The virus was used to infect NIH/3T3 cells and U87MG cells ($1 \times 10^5$). 6 μg/mL Polybrene (Sigma Chemical, USA) was added during the infection. The cell clones were examined by western blot. One hundred cells were plated. 6 monclonal cells were picked and examined by western blot again. The clones with the same expression abundance were selected for the next experiments.

Figure 3A:
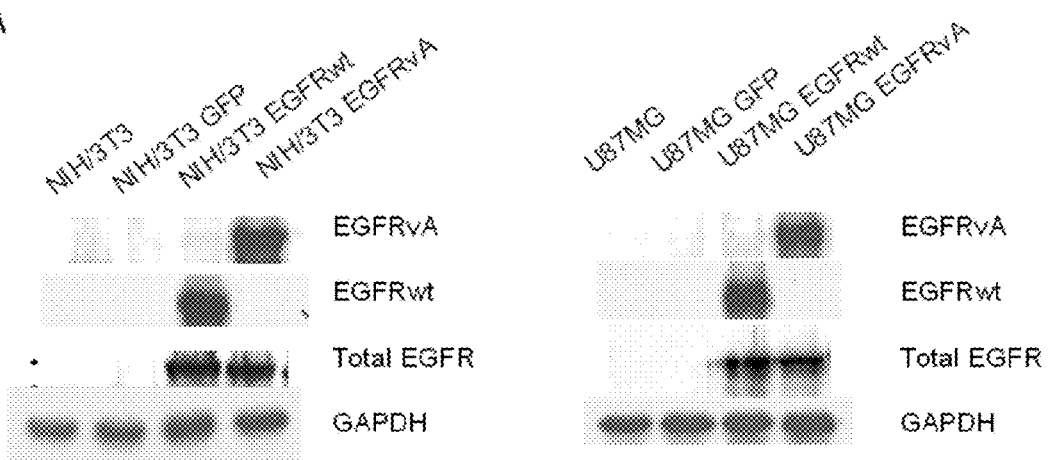
FIG. 3 shows the establishment and analysis of cell lines with stable EGFRvA expression, wherein, 3A represents Western blot; 3B represents: FACS.
Figure 3B:
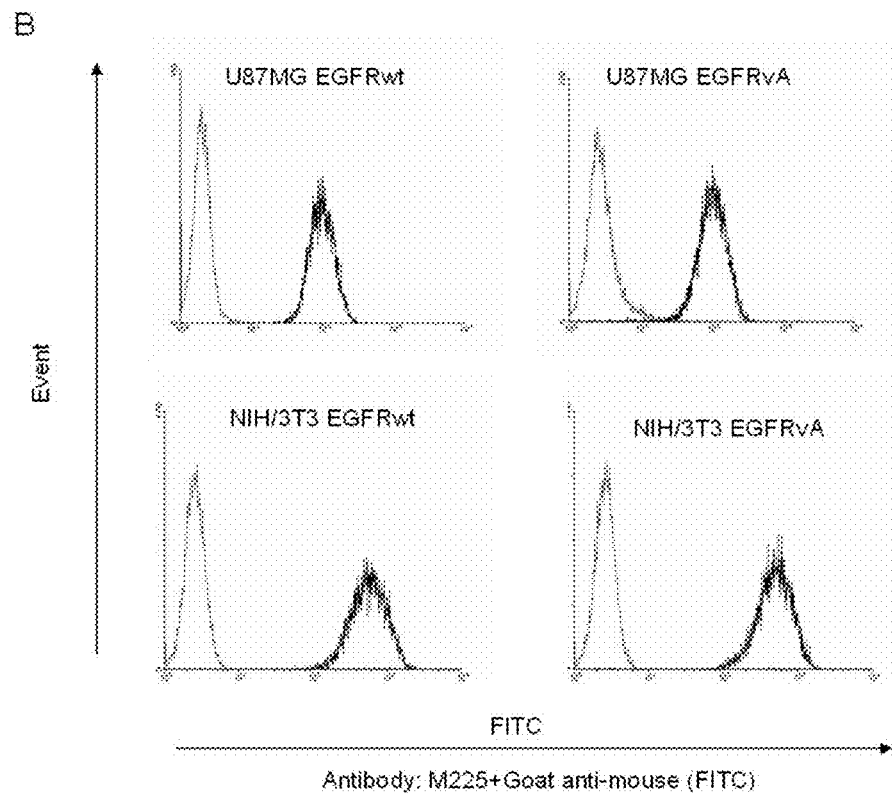

Results: U87MG EGFRwt and U87MG EGFRvA cell strains with relatively the same expression level were obtained. The total EGFR expression levels in NIH/3T3 EGFRwt cell line and in NIH/3T3 EGFRvA cell line were also similar (FIG. 3A).

EXAMPLE 6

FACS Assay $1 \times 10^6$ cells of NIH/3T3 EGFRwt/NIH/3T3 EGFRvA and U87MG EGFRwt/U87MG EGFRvA candidate clones were collected respectively. The cells were resuspended using 10 mmol EDTA and incubated with anti-EGFR antibodies (mouse monoclonal antibody M225, the dilution 1:100) and the nonrelevant isotype antibody respectively at room temperature for 1 hour. After that, secondary antibody (goat anti-mouse-FITC diluted 1:50) was added and incubated at room temperature for 30 min. The samples were collected and analyzed with BD FACSCalibur.winMDI2.9 software was used to process the obtained data and plotting.

Results: We found that the total EGFR expression levels in the U87MG EGFRwt and U87MG EGFRvA were almost the same. The total EGFR expression level in the NIH/3T3 EGFRwt and NIH/3T3 EGFRvA cell line were also almost the same. All of the four cell lines are single clonal.

EXAMPLE 7

Cell Proliferation Assay

Materials: CCK-8 kit purchased from Dojindo Laboratories

The cells in logarithmic growth phase were collected, counted and seeded in six 96-well plates by 300 cells per well. On each plate, each kind of cells was seeded in quintuplicate. One plate was taken every 24 h. The original culture medium was replaced with medium containing 10% CCK-8, incubated for another 2 h, and then OD450 value was measured, for 6 days in total. The cell growth curve was plotted.

Figure 4:
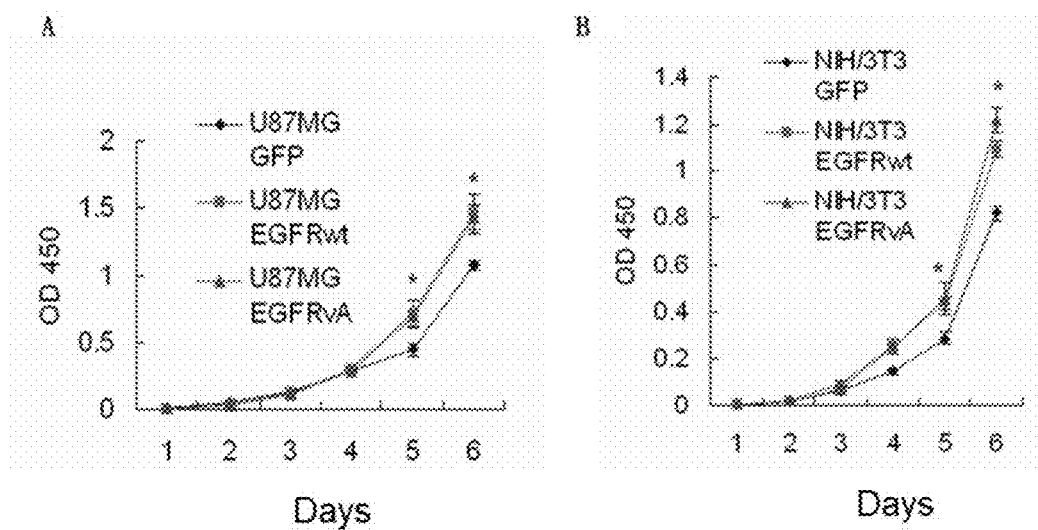
FIG. 4 shows that EGFRvA promotes cell proliferation in vitro.

The results were shown in FIG. 4: from the 5 day, U87MG cells with EGFRwt and EGFRvA over-expression display a stronger cell proliferation than U87MG GFP cells ($p<0.01$). There is no significant difference ($p>0.05$) between the proliferation ability of U87MG EGFRwt and that of U87MG EGFRvA cells. NIH/3T3 serial transfectants also showed the same results.

EXAMPLE 8

Cell migration and invasion assay

Materials: Transwell chambers (pore size: 8.0 μm) and Matrigel were purchased from BD Bioscience.

Method:

The scratch experiments: for primarily detecting the effect of EGFRvA on cell migration, NIH/3T3 stable transfectants were selected in scratch experiments. The cells in logarithmic growth phase were collected, counted and then seeded in 6-well plate by $1 \times 10^6$ cells per well. The cells were cultured to 100% confluence. Sterile yellow Tip was used to draw scratches at a width of about 1 mm on the cell layer. The cells were washed 3 times with serum-free medium to remove cells detached by the scratch. Photographes were taken respectively at 24 h, 48 h and 72 h under a microscope and the migrated cells were counted.

Transwell migration assay: formore accurately detecting the effect of EGFRvA on cell migration, the transwell migration experiment was performed. $5 \times 10^4$ cells were resuspended in 200 μl of serum-free culture medium and seeded into upper chamber of the Transwell. 600 μl of 10% FBS-containing culture medium were added into the lower chamber of the Transwell. The cells were culture for 12h (NIH/3T3 GFP, NIH/3T3 EGFRwt, NIH/3T3 EGFRvA) or 24 h (U87MG GFP, U87MG EGFR, U87MG EGFRvA), and then fixed by 4% polyformaldehyde for 1 h. Cells without migration in the upper chamber of the Transwell were wiped away with a cotton swab. The remaining cells were stained with 0.1% crystal violet for 30 minutes, photographed under the microscope (100× magnification), and counted.

Cell invasion assay (Transwell invasion assay): for detecting the effect of EGFRvA on cell invasion, cell invasion assay was performed. 100 μl of Matrigel diluted to 1 μg/μl was plated in the upper chamber of the Transwell and Incubated at 37° C. for 4 h. Serum-free medium was used to wash Matrigel twice. $1 \times 10^5$ cells were counted, resuspended in 200 μl of serum-free culture medium, and added to Transwell upper chamber paved with Matrigel. To the lower chamber was added with 600 μl of culture medium containing 10% FBS and incubated for 24 h. The cells were fixed by 4% polyformaldehyde for 1 h. Cells in the upper chamber of the Transwell were wiped away with a cotton swab. The remaining cells were stained with 0.1% crystal violet for 30 minutes, photographed under the microscope (100× magnification), and counted.

Figure 5:
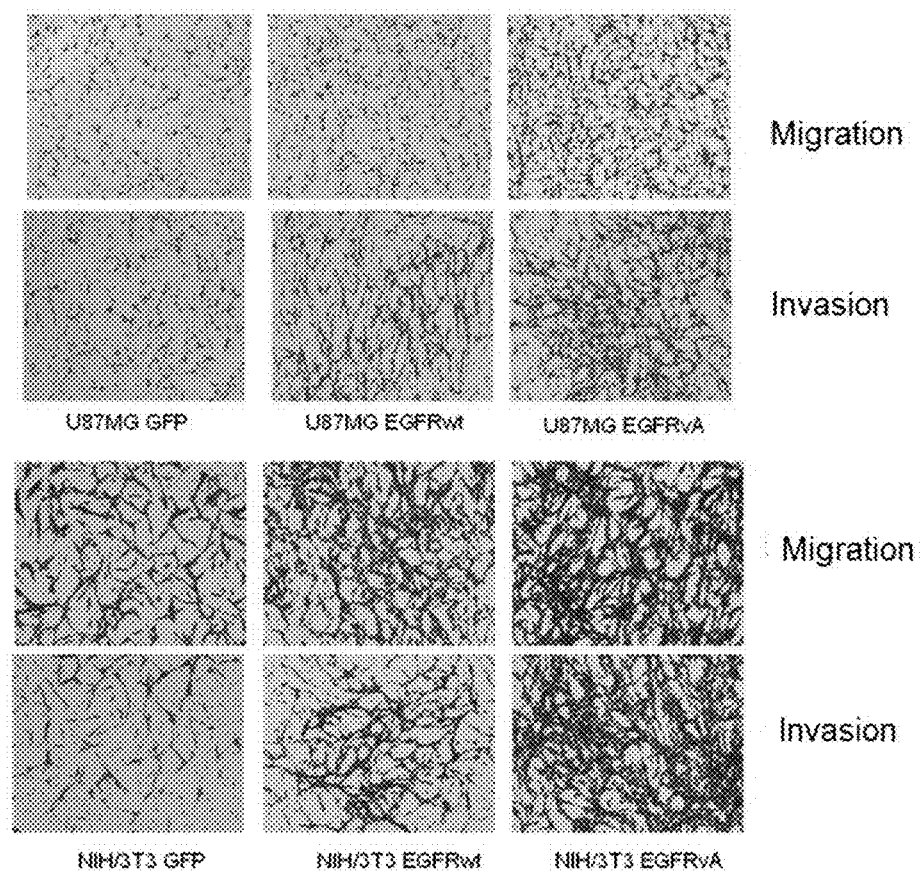
FIG. 5 shows that EGFRvA promotes cell invasion and migration in vitro.

Results: 24 to 72 hours after the scratch, compared with NIH/3T3 GFP control cells, NIH/3T3 EGFRwt cells and NIH/3T3 EGFRvA cells display significant migration capacity while the NIH/3T3 EGFRvA cells have relatively stronger migration ability (p<0.05). Transwell experiments showed more obvious results, that is, both in mouse fibroblast cell line NIH/3T3 or in human glioma cell lines U87MG, EGFRvA have the stronger migration- and invasion-promoting capacity than EGFRwt (Table 2 and FIG. 5).

TABLE 2

EGFRvA has stronger migration- and invasion-promoting capacity than EGFRwt

|  | Migrated cells | | Invasive cells | |
| --- | --- | --- | --- | --- |
|  | EGFRwt/ GFP | EGFRvA/ EGFRwt | EGFRwt/ GFP | EGFRvA/ EGFRwt |
| U87MG | 1.93 | 2.42 | 4.40 | 1.81 |
| NIH/3T3 | 2.68 | 1.61 | 2.91 | 1.98 |

EXAMPLE 9

In vivo metastasis assay 6-8 weeks old nude mice were taken and divided into three groups with 10 in each group. $1\times10^6$ cells (U87MG-GFP, U87MG EGFRwt and U87MG EGFRvA cell lines) per mouse were injected into the three groups of mice via tail vein. MicroCT scan was performed 18 days later. The body weight of the mice was measured at the day before tumor inoculation and sacrification respectively. After the body weight was measured, the mice were sacrificed and the lung was weighed. Immunohistochemistry assay was performed on the isolated tissues. SPSS 11.0 was selected as Data processing software. The homogeneity of variance between groups was proved firstly through lenvene test and then variance test was applied to verify whether there is overall significant difference among the groups. Finally, the LSD test was used in pairwise comparisons between groups.

Figure 6:
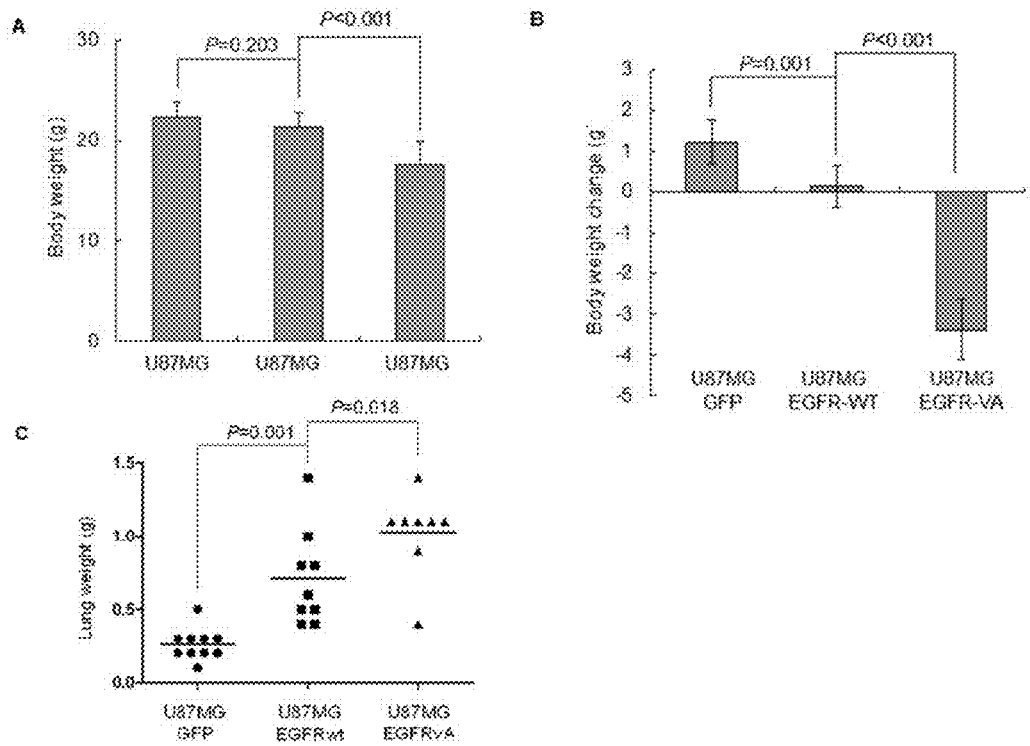
FIG. 6 shows that EGFRvA promotes U87 cell metastasis in lung in vivo. Wherein, A shows the body weight of the mice with tumor xenografts; B shows the change of the body weight in the mice with tumor xenografts; C shows the weight of the lung in the mice with tumor xenograts. *: P<0.05, **: P<0.01
Figure 7:
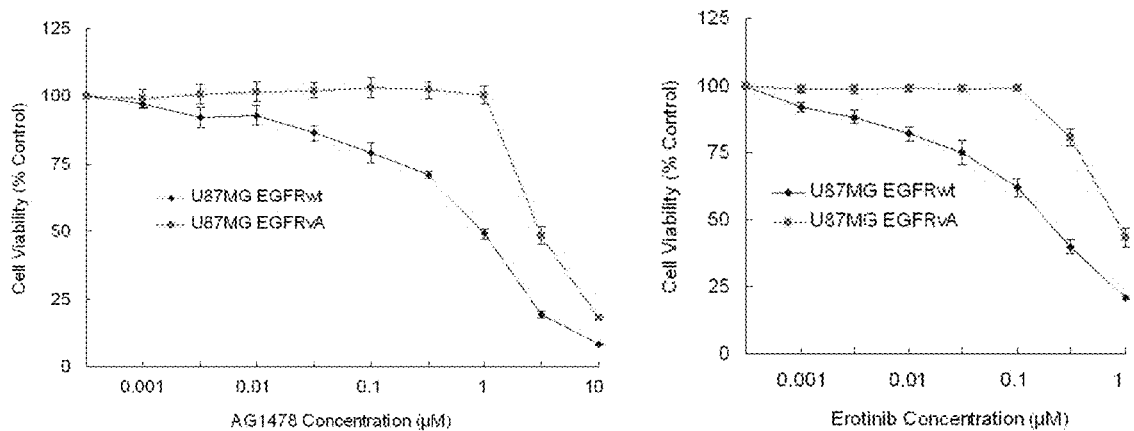
FIG. 7 shows that the cell line expressing EGFRvA stably displays the lower sensitivity to erlotinib, an EGFR inhibitor, compared with the cell line expressing EGFR stably.

Results: We observed that EGFRvA has stronger metastasis-promoting capacity than EGFR. This was demonstrated in the change of lung or body weight in the mice. The lung of the mice inoculated with U87MG-GFP has occasional nodules while keep the basic mophorlogy while the lung in the mice inoculated with EGFRwt or EGFRvA transfectants has much more nodules. After visual observation and immunohistochemistry determination, the lung in the mice inoculated with EGFRvA transfectants has more tumor invasion than those in the mice inoculated with EGFRwt. Actually, lung weight of the mice in the EGFRwt group (P=0.001) and EGFRvA group (P<0.001) significantly higher than that in U87MG-GFP group while the lung weight in the EGFRvA group is higher than that of EGFRwt group (P=0.018). The physiological condition of the EGFRvA group is also the worst among the three groups. The body weight of the mice in EGFRvA group is significantly lighter than GFP group and EGFRwt group (P<0.001). From the change of the body weight, the same conclusion can be obtained (P<0.001). The above evidences strongly indicate that EGFRvA has stronger tumor cell invasion-promoting capacity than EGFRwt (FIG. 6).

EXAMPLE 10

Cell Growth Suppression Assay Using Small Molecular Inhibitors Against EGFR

Materials: AG1478 was purchased from Calbiochem while Erlotinib was purchased from Roche pharmaceutical inc.

Methods: cells in the log-phase growth were plated in 96-well plates with 3000 cells/well. After cultured for 24 h, Erlotinib or AG1478 at different concentrations were added and the cells were cultured for another 72 h. The medium were replaced with fresh medium containing 10% CCK-8 reagents and incubated for another 2 h. The OD450 value was then measured.

Results: The $IC_{50}$ values of Erlotinib and AG1478 on cells with EGFRvA expression are over 3-fold higher than those with EGFRwt expression, indicating EGFRvA has a stronger resistance to anti-EGFR small molecule inhibitors.

TABLE 3

EGFRvA is more resistant to anti-EGFR small molecular inhibitors

|  | $IC_{50}$ (μM) | |
| --- | --- | --- |
|  | AG1478 | Erlotinib |
| U87MG EGFRwt | 0.89 | 0.23 |
| U87MG EGFRvA | 4.06 | 0.84 |
| $IC_{50}$ ratio (EGFRvA/EGFRwt) | 4.56 | 3.65 |

EXAMPLE 11

Screening the Antagonists Against EGFRvA Polypeptide

According to the method said in example 8, the following two materials were applied to U87-EGFRvA cell line and then their effects on the cell migration were measured: (a) candidate materials; (b) blank control.

If the cell migration in the group (a) is statistically lower than that in the group (b), it indicates that the candidate materials are antagonists of EGFRvA polypeptide; if the cell migration in the group (a) is significantly higher than that in the group (b), than it indicate that the candidate materials are agonists of EGFRvA polypeptide.

Similarly, according to the method said in example 8, the following two materials was applied to MDA-MB-468 cells which has endogenous EGFRvA expression and then their effects on the cell migration were measured: (a) candidate materials; (b) blank control.

If the cell migration capacity in the group (a) is statistically lower than that in the group (b), it indicates that the candidate materials are antagonists of EGFRvA polypeptide; if the cell migration capacity in the group (a) is significantly higher than that in the group (b), than it indicates that the candidate materials are agonists of EGFRvA polypeptide.

EXAMPLE 12

The Expression and Purification of Recombinant EGFRvA Protein

The NIH3T3-EGFRvA positive clones were picked and amplified. The clones were washed twice with cold PBS (pH 7.4). Buffer A (2% Triton X-100 100 mM NaCl, 50 mM Hepes, 1 mM EGTA, 0.5 ug/ml Leupeptin, 20 uM pmsf pH=7.4) was added and incubated on ice for 15 min. The cell layer was scraped, centrifuged at 4° C., 10000 g, for 5 min. The supernatant was collected and filtered with 0.22 um membrane. The supernatant was purified using a CNBr-activated Sepharose 4B affinity chromatography conjugated with the anti EGFRvA antibody (1F3-52). After the columm was sufficiently washed with buffer B (0.5% Triton X-100 100 mM NaCl, 50 mM Hepes, 20 uM PMSF, 1 mM EGTA, pH=7.4) and eluted with buffer C (0.5% Triton X-100 100 mM NaCl, 100 mM citrate, 20 uM PMSF, 1 mM EGTA, pH=3.0), the eluate was collected and ⅒ volume of 1 M Tris HCl (pH 9.6) solution was added to neutralize the eluate, thereby obtaining the human EGFRvA proteins.

EXAMPLE 13

Preparation of Antibody Against EGFRvA Protein

The recombinant human EGFRvA protein obtained in Example 12 was used to immunize animals to produce antibodies. Specific methods are as follows. The recombinant molecule was isolated by chromatography. The reombinant molecule can also be separated by SDS-PAGE gel electrophoresis method. The electrophoretic bands were excised from the gel, and emulsified with an equal volume of complete Freund's adjuvant. Mice were injected intraperitoneally with 50-100 μg/0.2 ml emulsified protein. 14 days later, the same antigen was emulsified with incomplete Freund's adjuvant. The mice were injected intraperitoneally with a dose of 50-100 μg/0.2 ml emulsified antigen in order to boost the immunization. The immunization was boosted once every other 14 days for at least three times. The specific reactivity of the antiserum obtained was assessed by its capacity for precipitating the translation product of human EGFRvA Protein gene in vitro. The results showed that the antibody can specifically bind to the protein of the invention.

EXAMPLE 14 shRNA Interference Experiments

Specific sequences were designed according to the 3'-specific sequence of EGFR-WT and EGFR-VA.
Specific interference sequence for EGFR-WT:

```
                                       (SEQ ID NO: 17)
5'-GCCACAAAGCAGTGAATTTATTCAAGAGATAAATTCACTGCTTTGT

GGCTTTTT-3'.
```

Specific interference sequence for EGFR-VA:

```
                                       (SEQ ID NO: 18)
5'-GAGCAGCCAGTCTCCAGTGTCCAATCAAGAGTTGGACACTGGAGAC

TGGCTGCTTTTT-3'
```

Mock control sequence (random primers):

```
                                       (SEQ ID NO: 19)
5'-GTCTCCGAACGTGTCACGTTCAAGAGACGTGACACGTTCGGAGACT

TTTT-3'.
```

All DNA sequences were artificially synthesized and cloned into the pLV-THM plasmid. The successfully cloned vectors were used to co-transfected 293T cells with the packaging plasmid psPAX2 as well as pMD2.G. The viral supernatant was collected and used to infect the target cells. Because pLV-THM comprised EGFP gene, green fluorescence can be observed in the cells successfully infected. The results of the interference can be validated with RT-PCR and Western Blot.

Figure 8:
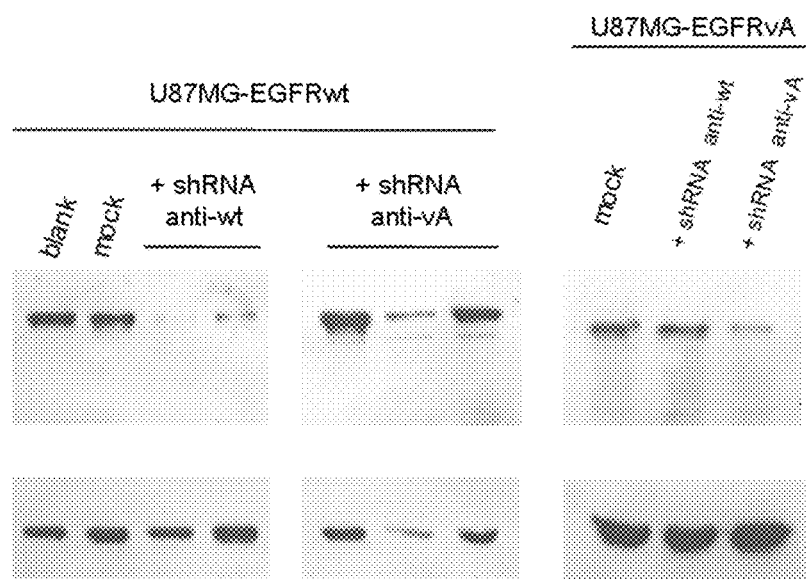
FIG. 8 shows the detection of the specificity of the shRNA, indicating that the selected shRNA can specifically interfere the target sequence; wherein, Mock is the random primer control; B is blank control.

Results:

As shown in FIG. 8, the efficacy and specificities of shRNA-antiWT and shRNA-antiVA were detected in model cell lines, U87MG EGFR-WT and U87MG EGFR-VA cells. The results indicated that both shRNA-antiWT and shRNA-antiVA can knock down the target gene in the model cell lines. Besides, no cross interference between the two shRNAs was observed.

Figure 9:
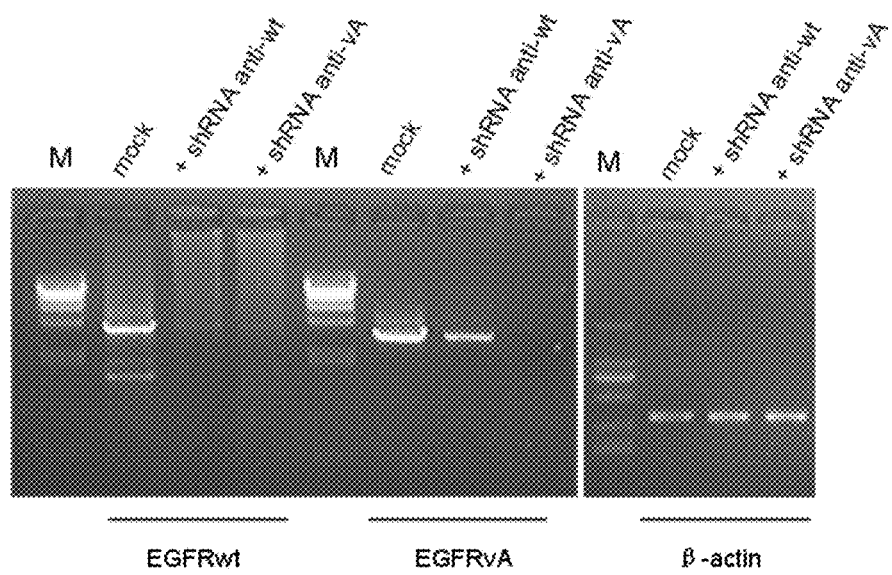
FIG. 9 shows that the selected shRNA can efficiently inhibit the corresponding EGFR mRNA expression in the H1299 cells. Wherein, Mock is the random primer control.

As shown in FIG. 9, when using shRNA-antiWT and shRNA-antiVA to knock down the target gene (EGFRwt and EGFRvA respectively) in the H1299 cells, the shRNA also downregulated the mRNA level of the other EGFR isoform.

Figure 10:
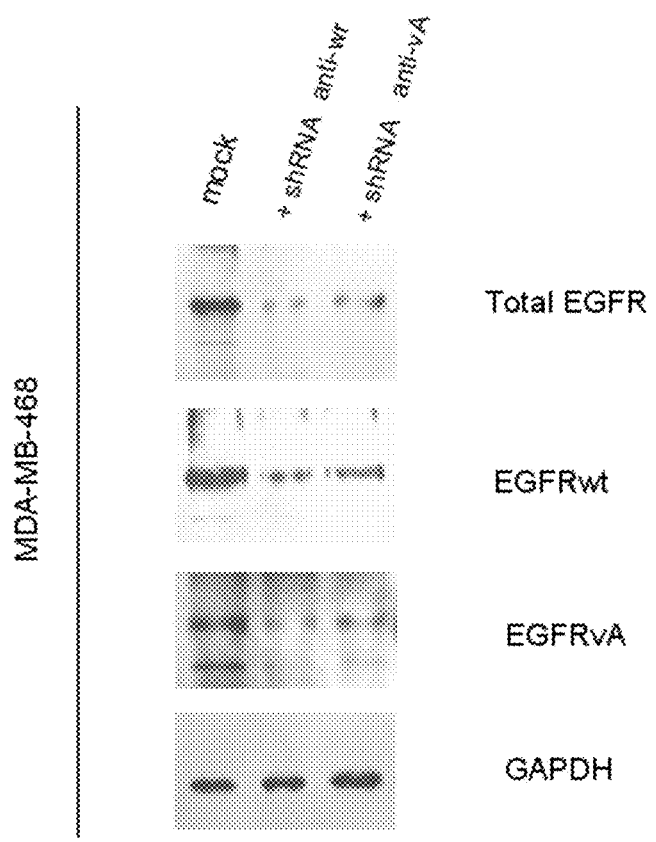
FIG. 10 shows that in MDA-MB-468 cells, the selected shRNA can efficiently inhibit the expression of the corresponding EGFR polypeptide.

As shown in FIG. 10: to further prove the above results, the same gene knock-down was also performed in MDA-MB-468 cells and the protein leve was also detected by Western blot. The results obtained are similar to those in H1299 cells. Both the shRNAs can not only interfere the target gene but also downregulate the expression of the other EGFR isoform. Given that we have rule out the off target possibility of the shRNA using the model cell lines, there must be other mechanisms resulting in the synchronical downregulation of EGFR-WT and EGFR-VA in H1299 and MDA-MB-468 cells.

All literatures mentioned in the present application are incorporated by reference herein, as though individually incorporated by reference. Additionally, it should be understood that after reading the above teachings, many variations and modifications may be made by the skilled in the art, and these equivalents also fall within the scope as defined by the appended claims.

Reference

1) Ullrich A. et al. Human Epidermal Growth Factor Receptor cDNA Sequence and Aberrant Expression of the Amplified Gene in A431 Epidermoid Carcinoma Cells. Nature, 1984, 309: 418-425

2) Downward et al. Close similarity of Epidermal Growth Factor Receptor and v-erb B oncogene Protein Sequence. Nature 1984, 307: 521-527, 3) Libermann et al. Amplification, Enhanced Expression and Possible Rearrangement of EGF Receptor Gene in Primary Human Brain Tumors of Glial Origin. Nature 1985, 313: 144-147

4) Wong et al. Increased Expression of the Epidermal Growth Factor Receptor Gene in Malignant Gliomas is Invariably Associated with Gene Amplification. Proc. Natl. Acad. Sci. USA. 1987, 84:6899-6903.

5) Yamazaki et al. Amplification of the Structurally and Functionally Altered Epidermal Growth Factor Receptor Gene (c-erbB) in Human Brain Tumors. Molecular and Cellular Biology 1988, 8:1816-1820.

6) Maiden et al. Selective Amplification of the Cytoplasmic Domain of the Epidermal Growth Factor Receptor Gene in Glioblastoma Multifome. Cancer Research 1988(4): 2711-2714.

7) Modjtahedi H, and Dean C. The receptor for EGF and its ligands Expression, prognostic value and target for therapy in cancer. International Journal of Oncology 1994 (4): 277-296.

8) Fung YKT, et al. Activation of the Cellular Oncogene c-erb B by LTR Insertion: Molecular Basis for Induction of Erythroblastosis by Avian Leukosis Virus. Cell 1983, 33:357-368

9) Yamamoto et al. A New Avian Erythroblastosis Virus, AEV-H Carries erbB Gene Responsible for the Induction of Both Erythroblastosis and Sarcoma. Cell 1983,34:225-232

10) Nilsen et al. c-erbB Activation in ALV-Induced Erythroblastosis: Novel RNA Processing and Promoter Insertion Results in Expression of an Amino-Truncated EGF Receptor. Cell 1985, 41: 719-726

11) Gammett et al. Differences in Sequences Encoding the Carboxy-Terminal Domain of the Epidermal Growth Factor Receptor Correlate with Differences in the Disease Potential of Viral erbB Genes."Proc. Natl. Acad. Sci. USA 83:6053-6057(1986)

12) Gilmore et al. Protein Phosphorylation at Tyrosine is Induced by the v-erb B Gene Product in Vivo and in Vitro. Cell, 1985,40:609-618, (1985)

13) Kris et al. Antibodies Against a Synthetic Peptide as a Probe for the Kinase Activity of the Avian EGF Receptor and v-erbB Protein. Cell, 40:619-625(1985)

14) Nilsen et al. c-erbB Activation in ALV-Induced Erythroblastosis: Novel RNA Processing and Promoter Insertion Results in Expression of an Amino-Truncated EGR Receptor. Cell, 1985,41:719-726

15) Raines et al. c-erbB Activation in Avian Leukosis Virus-Induced Erythroblastosis: Clustered Integration Sites and the Arrangement of Provirus in the c-erbB Alleles. Proc. Natl. Acad. Sci. USA,1985, 82:2287-2291

16) Pelley et al. Proviral-Activated c-erbB is Leukemogenic but not Sarcomagenic: Characterization of a Replication-Competent Retrovirus Containing the Activated c-erbB. Journal of Virology 1988, 62: 1840-1844

17) Wells et al. Genetic Determinant of Neoplastic Transformation by the Retroviral Oncogene v-erbB. Proc. Natl. Acad. Sci. USA 1988, 85:7597-7601

18) Yamazaki et al. Amplification, Enhanced Expression and Possible Rearrangement of EGF Receptor Gene in Primary Human Brain Tumours of Glial Origin. Nature 1985, 313: 144-147;

19) Wikstrand C J, et al. Monoclonal antibodies against EGFRvIII are tumor specific and react with breast and lung carcinomas malignant gliomas. Cancer Research 1995, 55(14): 3140-3148

20) Olapade-Olaopa E O, et al. Evidence for the differential expression of a variant EGF receptor protein in human prostate cancer. Br J Cancer. 2000, 82(1):186-94

21) Ge H, et al. Evidence of High incidence of EGFRvIII expression and coexpression with EGFR in human invasive breast cancer by laser capture microdissection and immunohistochemical analysis. Int J cancer. 2002, 98(3):357-61

22) Moscatello G., et al. Frequent expression of a mutant epidermal growth factor receptor in multiple human tumors. Cancer Res. 55(23):5536-9(1,995)

23) Garcia de Palazzo, I E., et al. Expression of mutated epidermal growth factor receptor by non-small cell lung carcinomas. Cancer Res. 1993, 53(14):3217-20

24) Moscatello, G. et al, Evidence for the differential expression of a variant EGF receptor protein in human prostate cancer. Br J Cancer. 2000, 82(1):186-94

25) Wang H., et al. Epidermal growth factor receptor vIII enhances tumorigenicity and resistance to 5-fluorouracil in human hepatocellular carcinoma. Cancer Lett. 2009;279 (1): 30-8.

What is claimed is:

1. An isolated epidermal growth factor receptor variant A (EGFRvA) polypeptide, wherein the polypeptide comprises the amino acid sequence of SEQ ID NO: 2.

2. The polypeptide of claim 1, wherein the polypeptide consists of SEQ ID NO: 2.

3. A pharmaceutical composition comprising the polypeptide of claim 1 and a pharmaceutically acceptable excipient.

* * * * *